United States Patent
Shiki et al.

(10) Patent No.: US 6,450,961 B1
(45) Date of Patent: Sep. 17, 2002

(54) ULTRASOUND IMAGING USING FLASH ECHO IMAGING TECHNIQUE

(75) Inventors: Eiichi Shiki, Otawara; Yoshitaka Mine, Tochigi-Ken, both of (JP)

(73) Assignee: Kabushiki Kaisha Toshiba, Kawasaki (JP)

( * ) Notice: Subject to any disclaimer, the term of this patent is extended or adjusted under 35 U.S.C. 154(b) by 14 days.

(21) Appl. No.: 09/587,611

(22) Filed: Jun. 5, 2000

(30) Foreign Application Priority Data

Jun. 3, 1999  (JP) .......................................... 11-157085

(51) Int. Cl.⁷ ................................................. A61B 8/14
(52) U.S. Cl. ...................................................... 600/458
(58) Field of Search ................................ 600/437, 440, 600/441, 443, 447, 453–458

(56) References Cited

U.S. PATENT DOCUMENTS

| | | | |
|---|---|---|---|
| 5,188,113 A | * 2/1993 | Sato et al. | 600/455 |
| 5,694,937 A | 12/1997 | Kamiyama | |
| 5,785,654 A | * 7/1998 | Iinuma et al. | 600/441 |
| 5,993,391 A | * 11/1999 | Kamiyama | 600/443 |
| 6,080,107 A | * 6/2000 | Poland | 600/458 |
| 6,110,120 A | * 8/2000 | Holley et al. | 600/458 |
| 6,149,597 A | * 11/2000 | Kamiyama | 600/458 |

FOREIGN PATENT DOCUMENTS

| | | |
|---|---|---|
| JP | 8-280674 | 10/1996 |
| JP | 11-137550 | 5/1999 |

* cited by examiner

*Primary Examiner*—Marvin M. Lateef
*Assistant Examiner*—Ali M. Imam
(74) *Attorney, Agent, or Firm*—Oblon, Spivak, McClelland, Maier & Neustadt, P.C.

(57) ABSTRACT

A diagnostic ultrasound apparatus is provided for obtaining an image of an object into which an ultrasound contrast agent is injected. The apparatus has a transducer 1 for transmitting and receiving an ultrasound wave to and from the object and transmitting means (2, 81, 83) transmitting an ultrasound pulse into the object by driving the transducer under a first transmitting condition exerting a given destruction capability on the ultrasound contrast agent and a second transmitting condition having a destruction capability lower than that of the first condition. First image producing (3, 5) receive an ultrasound echo of the ultrasound pulse transmitted under the first transmitting condition and produce a first color-displayed image based on phase displacement information about the ultrasound echo. Additionally, second image producing means (3, 4) receive an ultrasound echo of the transmitted ultrasound pulse and produce a second image based on amplitude information about the ultrasound echo. The first and second images are displayed by display means (6, 82). According to this diagnostic ultrasound apparatus, for imaging a CFM image based on a flash echo phenomenon caused in an object in which a contrast agent injected, one interval during which the phenomenon will be caused and the other interval during which it will not be caused can be determined appropriately and images can be displayed effectively over those intervals.

47 Claims, 25 Drawing Sheets

(a)

|  | 1 | 2 | ... | N−1 | N |
|---|---|---|---|---|---|
| 1 | 1 | L+1 |  | (N−2)L+1 | (N−1)L+1 |
| 2 | 2 | L+2 |  | (N−2)L+2 | (N−1)L+2 |
| 3 | 3 | L+3 |  | (N−2)L+3 | (N−1)L+3 |
| ⋮ |  |  |  |  |  |
| L | L | 2L |  | (N−1)L | NL |

ORDER OF WRITING · DEPTH ↓ · TRANSMISSION/RECEIVING NUMBER (TIMES) → · (OLD) ← TIME → (NEW)

(b)

|  | 1 | 2 | ... | N−1 | N |
|---|---|---|---|---|---|
| 1 | N | N−1 |  | 2 | 1 |
| 2 | 2N | 2N−1 |  | N+2 | N+1 |
| 3 | 3N | 3N−1 |  | 2N+2 | 2N+1 |
| ⋮ |  |  |  |  |  |
| L | LN | LN−1 |  | (L−1)N+2 | (L−1)N+1 |

DEPTH ↓ · TRANSMISSION/RECEIVING NUMBER (TIMES) → · ORDER OF READING · (OLD) ← TIME → (NEW)

ULTRASOUND IMAGING USING FLASH ECHO IMAGING TECHNIQUE

BACKGROUND OF THE INVENTION

1. (Field of the Invention)

The present invention relates to a diagnostic ultrasound apparatus, and in particular, a diagnostic ultrasound apparatus capable of performing imaging known as flash echo imaging (FEI) involving the injection of an ultrasound contrast agent into an object.

2. (Description of Prior Art)

An ultrasound diagnostic apparatus has now become an indispensable modality in clinical sites, because, in addition to display images in real time, they have advantages of relatively low in cost, no exposure of X-rays, and allowing blood flow imaging based on an ultrasound Doppler technique.

Particularly, this blood flow imaging, which is a function that is effective in finding lesions in the cardiac system or others, is known as a technique of color flow mapping CFM or color Doppler tomography and is provided as a standard option in most apparatuses.

As widely known, this display requires that the same raster location (direction) of an object be ultrasound-scanned a plurality of N times to acquire time-sequential echo signals and those echo signals undergo the detection of velocities of blood cells at a desired depth position based on the Doppler technique. That is, obtaining a Doppler signal requires the same raster location to be scanned repeatedly at certain intervals. Based on phase shift amounts (Doppler shift amounts) of per unit time obtained from a reflected signal from the blood cells, blood flow velocities can be obtained.

An echo signal resulting from each time of ultrasound scanning contains a reflection wave from objects in motion such as blood cells and a reflection wave from fixed objects almost stationary, such as a blood vessel wall or organic parenchyma. Additionally it is characteristic that the latter is a dominant in terms of reflection intensity, and further, Doppler shifts are caused in the former but not almost caused in the latter (clutter signal). Thus, a Doppler signal is extracted from the echo signal by a quadrature phase detector, and a clutter component is eliminated by an MTI filter from the Doppler signal on the basis of differences in the Doppler shifts, thereby a blood flow Doppler signal being detected efficiently. This blood flow Doppler signal is then subjected to frequency analysis with its N-piece Doppler data at each depth position, thereby a mean of its spectrum (Doppler frequency), dispersion amount, and/or intensity (power) reflected from blood cells being calculated. These pieces of blood flow information are two-dimensionally displayed on a monitor, normally, with a B-mode image placed as a background.

Recently, a technique has eagerly been tried that an ultrasound contrast agent is injected into an object's blood vessel to enhance scattering intensity of ultrasound for improving a diagnostic performance. Particularly, the performances of the contrast agent have noticeably been improved for the fast few years, such that contrast effects have been improved and the agent has been allowed to be injected from the vein, resulting in reduced invasiveness. It is expected that this kind of contrast agent become popular more. In association with this, there has been a need that a diagnostic ultrasound apparatus should have capability of performing diagnosis with making use of all the characters of the contrast agent that has been improving year by year. The background of this need will now be detailed.

An ultrasound contrast agent now under development consists mainly of a few microns of microbubbles. It has been known that these microbubbles easily collapse at almost as similar sound pressures as used for ordinary ultrasound diagnosis, and generates a higher-intensity harmonic corresponding to a harmonic of an ultrasound pulse when the collapse occurs, so that showing a higher contrast effect. An imaging technique called flash echo imaging (FEI) obtaining B-mode images utilizing this character is reported by, for example, a paper "Japanese Journal of Medical Ultrasonics, Vol.23, Supplement 1; June, 1996; 67–195, 67–196" (the first report). This paper reports that, after a full charge of microbubbles by temporarily stopping ultrasound radiation, re-radiating an ultrasound pulse will cause large amounts of luminance enhancement in a tomographic image (tomographic image based on a harmonic component) simultaneously with the radiation, then the echo diminish immediately after that enhancement. This phenomenon is referred to as a flash echo phenomenon.

As to a prior art reference between color flow mapping and an ultrasound contrast agent, a paper "Japanese Journal of Medical Ultrasonics, Vol.22, Supplement 2; November, 1995; 66–33" is reported (the second report). This paper reports that, when an operator operates a freezing button to temporarily stop to transmit an ultrasound wave into the lever of a rabbit into which an ultrasound contrast agent was injected, then starts again the scanning with operating the freezing button, which provides the on/off states of transmission, a mosaic color image can be obtained in a velocity mode of color flow mapping. In this report, an image on this phenomenon is called cavitation image. Also reported is that this color image cannot be obtained at sound pressures less than a certain amount.

It is considered that this cavitation image can be obtained due to the same phenomenon as the flash echo image. Namely, considered is that this paper shows the fact that the flash echo phenomenon occurs with the fundamental wave of an ultrasound pulse and be observable using the color flow mapping. This also suggests that tissue blood (perfusion), which could not be imaged by the conventional color flow mapping, can be imaged.

Furthermore, the fact that the flash echo phenomenon is observable with even harmonic CFM images is reported by a paper "Japanese Journal of Medical Ultrasonics, Vol.23, Supplement 2; November, 1996; 68–156" (the third report). Described in this paper is that, when the flash echo phenomenon occurs, a mosaic color image is obtained in the velocity mode of color flow mapping with a harmonic. Also reported by this paper is that a Doppler spectrum of a harmonic on the flash echo phenomenon is broad as shown in FIG. 21.

This means that the perfusion can be imaged as well and its color image is shown in a mosaic. In other words, since Doppler shifts seldom occur in a clutter component that is an echo reflected by organic parenchyma, this component can be eliminated by an MTI filter, but a harmonic on the flash echo phenomenon passes the MTI filter and is imaged in the end, even if the contrast agent is in motion (for example, in a blood vessel) or at rest (for example, perfusion), because of a broad band of its Doppler spectrum. Additionally, an average of a Doppler spectrum at each of spatial points differ from each other at random, resulting in a mosaic image.

By the way, taking the similarity between the above second and third reports into account, it is assumed that the Doppler spectrum of a fundamental wave on the flash echo phenomenon is also broad in band.

Further, another report on the contrast agent is made by papers "Japanese Journal of Medical Ultrasonics, Vol.23, Supplement 2; November, 1996; 68–157" and "Journal of Medical Ultrasonics, Vol.24, No.3; March, 1997; 69P3–5" (the fourth report). These reports explain spectrums on the flash echo phenomenon occurring in three types of contrast agent. From these spectrums reported, it has been found that the fundamental wave is higher than the harmonics in sensitivity given when the flash echo phenomenon occurs.

Further, there has been known that the intensity of an echo signal on the flash echo phenomenon reduces gradually with time until the microbubbles collapse entirely.

A summary from a clinical point of view can be given as follow: (1) Using the flash echo phenomena enables an ultrasound contrast agent to be detected highly sensitively, (2) the CFM method is usable for observing perfusion, and (3) the CFM method is visualized in color so as to be easy to understand, while the velocity mode is visualized as a mosaic color image so as to be easy for discrimination. From a technical point of view, (4) causing the flash echo phenomenon requires that the transmission of an ultrasound wave be halted temporarily, (5) the flash echo phenomenon will not basically occur at sound pressures smaller than a certain amount, (6) a signal on the flash echo phenomenon will diminish gradually in intensity until the microbubbles collapse entirely, (7) using the CFM method, the flash echo phenomenon is observable with either a fundamental wave or a harmonic, and (8) a Doppler spectrum shown when the flash echo phenomenon is caused is broad in band.

Thus, it is supposed that causing the flash echo phenomenon from a contrast agent injected into an object before producing the enhanced signals into a color-mapping image leads to supply of clinically effective images.

However, in the conventional diagnostic ultrasound apparatus making use of the flash echo phenomenon, an ultrasound imaging technique that maximally shows the priorities of this phenomenon has not been established yet. Particularly, as to not only setting of an imaging interval during which the flash echo phenomenon is caused and a non-imaging interval but also image display techniques during those intervals, any effective measure has not been proposed yet.

Further, in the conventional diagnostic ultrasound apparatus having a function of color flow mapping, to cause the flash echo phenomenon requires that a freezing button be operated by hand to temporarily halt the transmission, then to release this frozen state after a certain time. This manual operation becomes complicated and it is difficult to establish accurate on/off intervals, thus being lowered in practicality. As a result, this manual setting is not adopted into actual fields of clinics at all.

On one hand, there is not always guarantee that various types of signal processing which have already been performed with the conventional color flow mapping are matched to the detection and processing of an enhanced signal due to the flash echo phenomenon. There is even a possibility that the detection has not been carried out so sensitively.

Namely, although it has been thought that color flow mapping imaging of an enhanced signal on the flash echo phenomenon might be effective, there has not been provided an apparatus that has a capability to display images, maneuverability, and detection sensitivity raised to the extent necessary to make use of the practicality of this imaging in actual clinical fields.

SUMMARY OF THE INVENTION

The present invention has been made in consideration of the drawbacks of the foregoing prior art techniques. A first object of the present invention is to, for imaging in color flow mapping a reflection signal associated with the flash echo phenomenon caused by a contrast agent injected into an object, be able to suitably determine one interval during which the flash echo phenomenon is caused and the other interval during which it is not caused, and be able to obtain clinically effective images through those intervals.

A second object of the present invention is, in addition to the above first object, to perform processing steadily appropriate for a reflected signal owing to the flash echo phenomenon, so that the signal can be detected highly sensitively.

In order to accomplish the above objects, a diagnostic ultrasound apparatus of the present invention, as one mode, is provided for obtaining an image of an object into which an ultrasound contrast agent is injected, and the apparatus features that it comprises: an ultrasound transducer for transmitting and receiving the ultrasound wave to and from the object; transmitting means (or a unit) for transmitting an ultrasound pulse into the object by driving the ultrasound transducer under a first transmitting condition exerting a given destruction capability on the ultrasound contrast agent and a second transmitting condition having a destruction capability lower than that of the first condition; first image producing means (or a unit) for receiving an ultrasound echo of the ultrasound pulse transmitted under the first transmitting condition and producing a first color-displayed image based on phase displacement information about the ultrasound echo; second image producing means (or a unit) for receiving an ultrasound echo of the transmitted ultrasound pulse and producing a second image based on amplitude information about the ultrasound echo; and means (or a unit) for displaying both the first and second images.

As another mode, it is featured that a diagnostic ultrasound apparatus for obtaining an image of an object into which an ultrasound contrast agent is injected, the apparatus comprises: an ultrasound transducer for transmitting and receiving the ultrasound wave to and from the object; transmitting means (or a unit) for transmitting an ultrasound pulse into the object by driving the ultrasound transducer under a first transmitting condition exerting a given destruction capability on the ultrasound contrast agent and a second transmitting condition having a destruction capability lower than that of the first condition; first image producing means (or a unit) for receiving an ultrasound echo of the ultrasound pulse transmitted under the first and second transmitting conditions and producing a first color-displayed image based on phase displacement information about the ultrasound echo; second image producing means (or a unit) for receiving the ultrasound echo and producing a second image based on amplitude information about the ultrasound echo; and means (or a unit) for displaying both the first and second images.

Still as another mode, it is featured that a diagnostic ultrasound apparatus for obtaining an image of an object into which an ultrasound contrast agent is injected, the apparatus comprises: an ultrasound transducer for transmitting and receiving the ultrasound wave to and from the object; transmitting means (or a unit) for transmitting an ultrasound pulse into the object by driving the ultrasound transducer under a first transmitting condition exerting a given destruction capability on the ultrasound contrast agent and a second transmitting condition having a destruction capability lower than that of the first condition; first image producing means (or a unit) for receiving an ultrasound echo of the transmitted ultrasound pulse and producing a first color-displayed image based on phase displacement information about the ultrasound echo; second image producing means (or a unit) for receiving an ultrasound echo of the ultrasound pulse transmitted under the first transmitting condition and producing a second image based on amplitude information about the ultrasound echo; and means (or a unit) for displaying both the first and second images.

Still as another mode, it is featured that diagnostic ultrasound apparatus for obtaining an image of an object into which an ultrasound contrast agent is injected, the apparatus comprises: an ultrasound transducer for transmitting and receiving the ultrasound wave to and. from the object; transmitting means (or a unit) for transmitting an ultrasound pulse into the object by driving the ultrasound transducer at changeable intervals under a transmitting condition exerting a given destruction capability on the ultrasound contrast agent; image producing means (or a unit) for receiving an ultrasound echo of the ultrasound pulse transmitted under the transmitting condition and producing the image based on both phase displacement information and amplitude information about the ultrasound echo; and display means (or a unit) for displaying the image.

According to the above configurations, a contrast agent is injected and an ultrasound pulse is transmitted via the probe under the first and second transmitting conditions. Under the first transmitting condition, microbubbles of the contrast agent, which are essential constituents, are collapsed to cause a flash echo phenomenon, thus providing an echo signal in which the phenomenon is strongly reflected. In contrast, under the second transmitting condition, the microbubbles are basically collapsed, thus providing an echo signal in which only the tissue and/or blood flows are influenced. Thus appropriate changeover and setting of those transmitting conditions allow the on- and off-states of the flash echo phenomenon to be controlled.

In producing images under the first transmitting condition, because an echo signal contains a high-intensity reflection signal, called a clutter, originated from organic parenchyma, the clutter is removed from the echo signal using means for discriminating a signal from the contrast agent, providing only a flash echo signal caused by the contrast agent. The signal from the contrast agent may be a signal containing a fundamental signal from the contrast agent or a harmonic signal from the contrast agent. The flash echo signal emanated from the contrast agent, which is obtained by the discrimination, is directly displayed or displayed as information obtained by calculating Doppler frequency (velocity), dispersion, power and/or others from the flash echo signal of the contrast agent. The transmission and reception is automatically controlled, resulting in that CFM images of the flash echo signal can be obtained readily to provide a useful diagnostic ultrasound apparatus.

As another aspect, under the second transmitting condition, monitoring transmission and reception are performed with a lower sound pressure determined not to cause a flash echo phenomenon, and these scanning results are displayed in a wide variety of modes. For instance, B-mode tomographic images and/or CFM images can be displayed. Alternatively, the transmission and reception can be stopped under the second transmitting condition.

Further, through an interval during which the flash transmission is an on-state under the first transmitting condition and a monitor interval during which the flash transmission is an off-state under the second transmitting condition, B-mode tomographic images and/or CFM images can be displayed. This permits CFM images of a flash echo signal to be obtained while monitoring an object in real time.

Accordingly, image information about a region to be diagnosed can be obtained during the off-interval of the flash transmission. In addition, a position of a region to be examined is easily decided and positions are resistant to being shifted even when waiting is done without performing flash echo imaging. In this way, a flash echo contrast agent examination can be performed while observing a region to be diagnosed in real time, and it is possible to provide a diagnostic ultrasound apparatus which can be used in a simple manner, with an excellent maneuverability, and with an improved diagnostic performance.

When a flash echo phenomenon occurs, the intensity of a flash echo signal begins to weaken little by little immediately after the occurrence. Thus, where the transmission and reception are performed a plurality of times along the same direction, the use of data obtained in an earlier stage of the data acquisition, which are higher in the intensity of a flash echo signal, leads to a higher sensitivity. In the case that means for discriminating the signal from the contrast agent use, for example, an MTI filter (clutter elimination means), Doppler signals acquired by a plurality of times of the transmission and reception are inputted into the MTI filter in the opposite order to that in the reception. This allows the data obtained in the earlier stage to be used, thereby improving the sensitivity.

Alternatively, means for discriminating the signal from the contrast agent are able to use means for calculating differences of signals adjoining to each other among a plurality of signals received through a plurality of times of the transmission and reception, a clutter component can be removed with signals obtained by at least two times of transmission and reception. This results in that data obtained in an earlier stage of the data acquisition can be used, thus increasing sensitivity.

Additionally, the transmission and reception for tomographic images can be conducted together with the transmission and reception for CFM images, so a CFM image of flash echo signals is superposedly represented on a tomographic image thus obtained. In this case, the transmission and reception of an ultrasound pulse for a signal from a contrast agent always precedes that for tomographic images. Thus it is avoided that higher-sensitivity data are consumed by only the transmission and reception of an ultrasound pulse for tomographic images. CFM images (blood flow color images) are also formed by using earlier-stage data, thus increasing sensitivity.

As described above, the present invention adopts a way of adapting various types of processing performed in the CFM technique to the flash echo imaging, so that a higher-sensitivity diagnostic ultrasound apparatus is provided in the examination with contrast agents.

BRIEF DESCRIPTION OF THE DRAWINGS

In the accompanying drawings:

FIG. 11 is an illustration of orders of writing and reading of data, which describes an inverse reading to an MTI filter;

DETAILED DESCRIPTION OF THE PREFERRED EMBODIMENTS

Hereinafter, embodiments of the present invention will now be described with reference to the accompanying drawings.

First Embodiment

Figure 1:
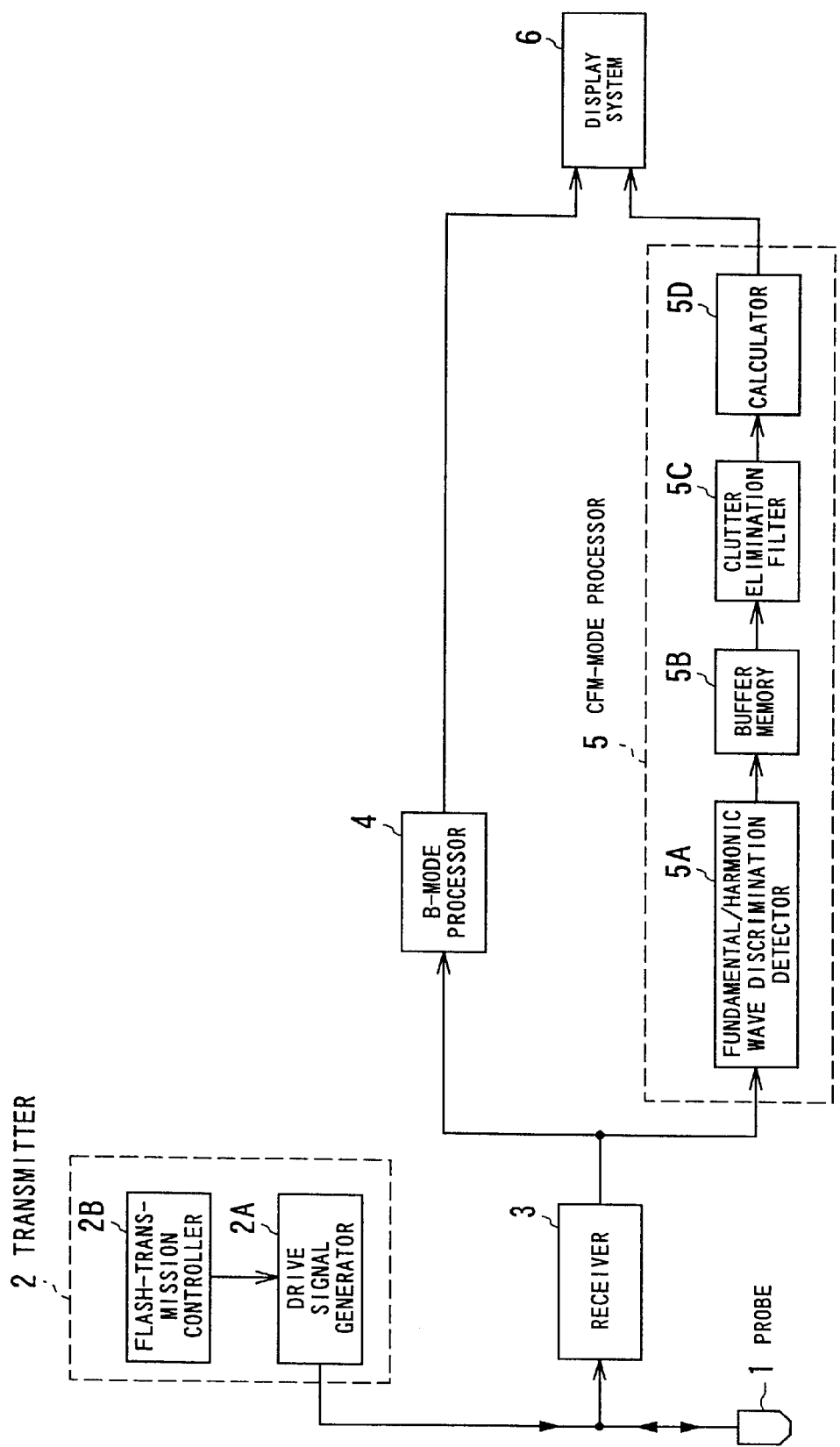
FIG. 1 is a functional block diagram of a diagnostic ultrasound apparatus according to a first embodiment of the present invention.

Referring to FIG. 1, a diagnostic ultrasound apparatus according to a first embodiment of the present invention will now be described.

The diagnostic ultrasound apparatus is used for diagnosis in which flash echo imaging (FEI) is performed in a CFM (color flow mapping) mode with an ultrasound contrast agent (hereafter called contrast agent), for example, vein-injected into an object to be diagnosed. As the contrast agent, "Levovist" (trade name) manufactured by Schering AG or "Optison" (trade name) manufactured by MBI can be used.

FIG. 1 shows a functional block diagram of the diagnostic ultrasound apparatus. As shown therein, the diagnostic ultrasound apparatus is provided with, in addition to an ultrasound probe (hereafter called probe) 1 contacted with the body surface of an object to be diagnosed, a display 2 and a receiver 3 both electrically connected with the probe 1, a B-mode processor 4 and a CFM-mode processor 5 both electrically connected with the receiver 3, and a display system 6 electrically connected with both of the processors 4 and 5.

The probe 1 has a function of bilaterally converting an ultrasound signal and an electric signal. One example of the probe 1 has an array type of piezoelectric transducers arranged in its tip. The array type of transducers has a structure in which a plurality of piezoelectric elements are arranged in parallel, where the arrangement direction is defined as a scanning direction. Each of the piezoelectric elements is assigned to each channel for transmission and reception.

The display 2 has a drive signal generator 2A generating a drive signal for exciting the transducers of the probe 1 and a flash-transmission controller 2B controlling a transmission state of flash echo imaging (FEI).

The flash-transmission controller 2B controls an on or off state of entire transmission and reception performed via the probe 1, by controlling the on and off-states of generation of a transmission trigger in the drive signal generator 2A. The flash echo imaging is conducted during only an interval of the on-state, but this imaging is stopped during an interval of the off-state.

The drive signal generator 2A operates during only the interval in which the transmission is set to the on state by the flash-transmission controller 2B. In this operation state of the generator 2A, the transducers of the probe 1 are transmission-delayed and driven in response to transmission triggers for a plurality of frames. For each drive, an ultrasound pulse is responsively transmitted from the probe 1 in a desired raster direction as a beam signal. This ultrasound pulse is transmitted at both a predetermined pulse repetition time Tr and a transmission frequency $f_0$.

In this on-state of transmission, ultrasound pulses for both the CFM and B modes are transmitted and received frame by frame responsively to the transmission triggers. In detail, at least a plurality of times of transmission and reception for the CFM mode is performed along the same raster direction, while one time of transmission and reception for the B mode is performed along the same raster direction. In this transmission and reception, the transmission is controlled such that the transmission for the CFM mode always precedes that for the B mode raster by raster. Thus, this prevents a situation in which the contrast agent has been no longer present at the positions on a raster when the CFM-mode transmission is carried out, due to the fact that the contrast agent was collapsed by the B-mode transmission.

When the contrast agent receiving the radiation energy of an ultrasound pulse transmitted from the probe 1 into an object, the microbubbles composing the agent collapse instantaneously, causing a flash echo phenomenon. A higher-intensity reflection component which occurs in the step of the phenomenon (which contains a fundamental wave corresponding to a transmission frequency of the ultrasound pulse, its harmonics, its sub-harmonics and super-harmonics) becomes a reflected ultrasound signal by being mixed with reflection components from other tissue, and at least part of the signal is received by the probe 1. When receiving the reflected ultrasound signal, each transducer of the probe 1 converts it into an identical electric-amount echo signal, and sends it to the receiver 3 (every reception channel).

Although not shown particularly, the receiver 3 amplifies the echo signal, A/D-converts the amplified echo signal, and delays the converted echo signal in a delay time pattern opposite to that in the transmission in every reception channel, before mutually adding the signals of all the reception channels. This gives the echo signal a directivity along a transmitted raster direction, and the echo signal is enhanced in that direction. Such beam-formed echo signal is then sent to the B-mode or CFM-mode processor 4 or 5 formed into a digital type of processor.

By the B-mode processor 4, the echo signal acquired by the transmission and reception of an ultrasound pulse for the B mode is detected, then produced into data of a B-mode tomographic image.

On one hand, the CFM-mode processor 5 has, as shown in FIG. 1, a fundamental/harmonic wave discrimination detector 5A, a buffer memory 5B, a clutter elimination filter 5C, and a calculator 5D. Of these, the echo signal is quadrature-phase-detected by the fundamental/harmonic wave discrimination detector 5A, thus Doppler data being extracted. One example is that a Doppler component corresponding to the fundamental wave (=transmission frequency $f_0$) of the ultrasound pulse is extracted from those Doppler data.

The Doppler data thus extracted are temporarily stored in the buffer memory 5B in an order of their inputs. And the Doppler data are read, at each position, from the memory 5B in the time sequential order opposite to that of data writing performed toward the same positions of a scanned cross section. That is, Doppler data are read sequentially from those in a later stage of those data where the effect of signal intensity enhancement thanks to the flash echo phenomenon has lessened. The read data are sent to the following clutter elimination filter 5C.

Using differences in the amounts of Doppler shifts, a clutter component emanating from stationary refractors is eliminated from the Doppler signal by the clutter elimination filter 5C. In this elimination, to avoid the influence of a transit response of the filter, data existing in an earlier stage of the filter output waveform are disposed of. The data that has been disposed of, however, do not all but contains the flash echo signal owing to the foregoing inverse reading of the echo data, and are not so significant, with the result that their disposal hardly has an influence on accuracy and sensitivity in analysis of velocity and power. In the calculator 5D, the echo data train (echo signal) thus-processed are subjected to analysis of velocity and/or power, and then to data production including a motion velocity image of the contrast agent, i.e., blood flows, a mosaic image inherent to a flash echo signal in perfusion (perfusion in living body's tissue), data of a CFM-mode image related to its velocity, and/or data of a power image of flows in blood vessels and/or perfusion. In order to prevent the directional separation of flows of the contrast agent from being inverted due to the foregoing data inverse reading, this calculator 5D has a function of correcting the directions.

The data produced by both of the B-mode and CFM-mode processors 4 and 5 are sent to the display system 6, in which, for example, a velocity-mapping color image or power image in the CFM mode is displayed on a B-mode tomographic image in a superposition manner.

Second Embodiment

Referring to FIGS. 2 to 12, a diagnostic ultrasound apparatus according to a second embodiment of the present invention will now be described. In this embodiment, the diagnostic ultrasound apparatus described in the first embodiment will now be detailed in terms of its configuration. The entire conceptual operation performed is similar to that in the first embodiment.

1. Outline of Apparatus Configuration

Figure 2:
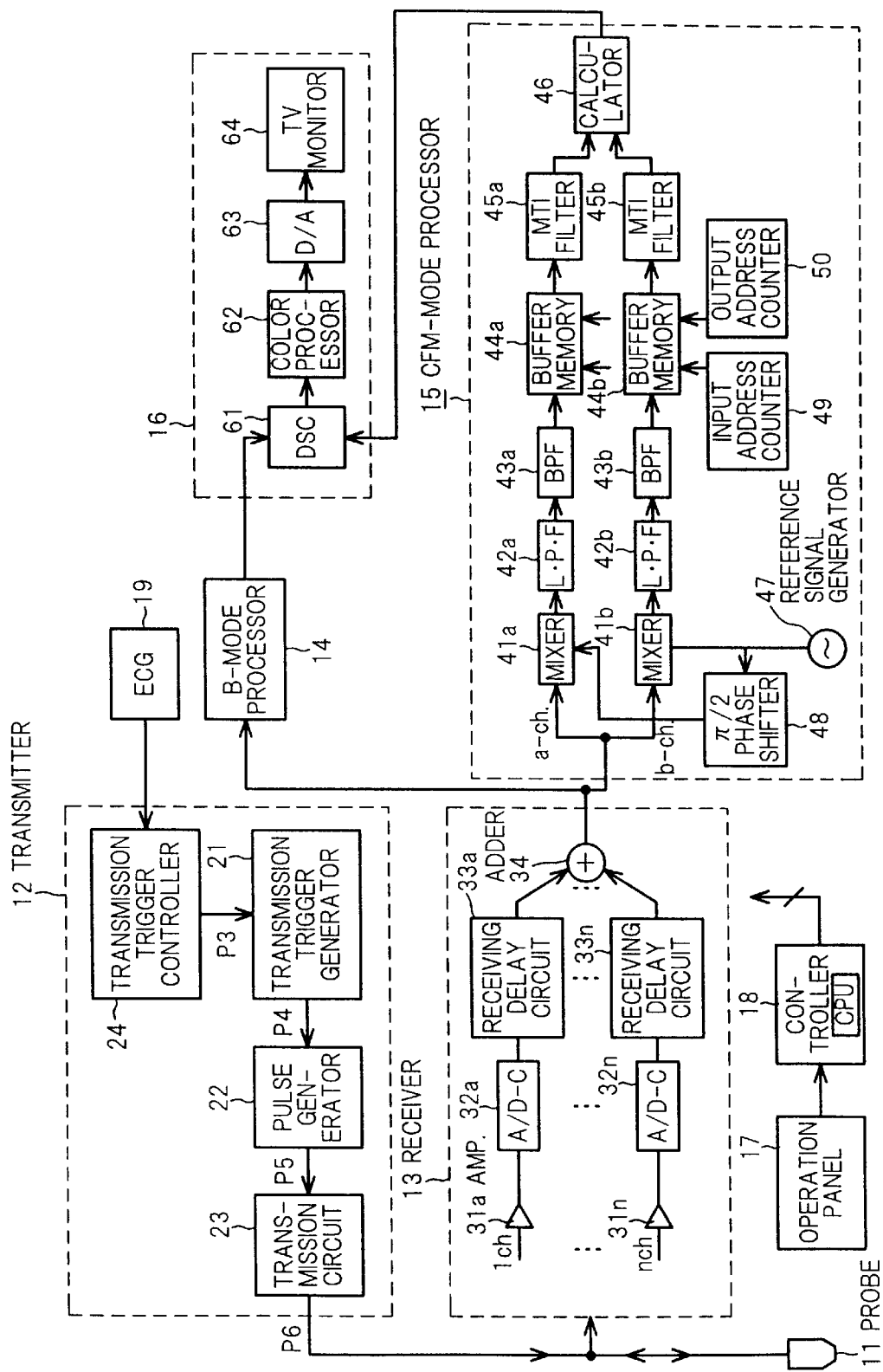
FIG. 2 is a block diagram showing the configuration of a diagnostic ultrasound apparatus according to a second embodiment of the present invention.

First, the configuration of this diagnostic ultrasound apparatus will be outlined. Similarly to the apparatus in the first embodiment, the diagnostic ultrasound apparatus shown in FIG. 2 is provided with, as a whole, a probe 11, transmitter 12, receiver 13, B-mode processor 14, CFM-mode processor 15, and display system 16. Additionally, the apparatus has an operation panel 17 used by an operator for inputting necessary information, a controller 18 for sending control information to predetermined units in the apparatus, and an ECG meter 19 for measuring an electrocardiograph (ECG) signal. The controller 18 has a CPU that carries out various types of calculation in software.

2. Configuration and Operation of Each Constituent

The probe 11 adopts, by way of example, a structure of electric sector scanning using an array type of transducers, like that in the first embodiment.

2.1. Configuration and Operation of Transmission System

The transmitter 12 comprises a transmission trigger generator 21 generating a transmission trigger, a pulse generator 22 generating a transmission pulse responsively to the reception of the transmission trigger, a transmission circuit 23 converting the transmission pulse to a drive pulse to give it to transducers of the probe 1, and a transmission trigger controller 24 controlling the operation of the transmission trigger generator 21.

Of these, the operations of both of the transmission trigger controller 14 and the transmission trigger generator 21 compose part of the characteristics of the present invention, which is therefore described as follows. An example of the configuration of the transmission trigger controller 24 will be described later.

First, the transmission trigger controller 24 is configured such that it controls the on-state (generation) and off-state (stop) of a transmission trigger used to the transmission trigger generator 21.

Transmitting an ultrasound pulse to a contrast agent causes a flash echo phenomenon, but after the phenomenon, the contrast agent disappears due to the collapse of its microbubbles. Thus it is necessary that transmission be stopped until succeeding microbubbles fill a region to be scanned to avoid the disappearance of the contrast agent. Re-starting the transmission at a time the microbubbles are fully stored gains a satisfactory flash echo phenomenon.

Figure 3:
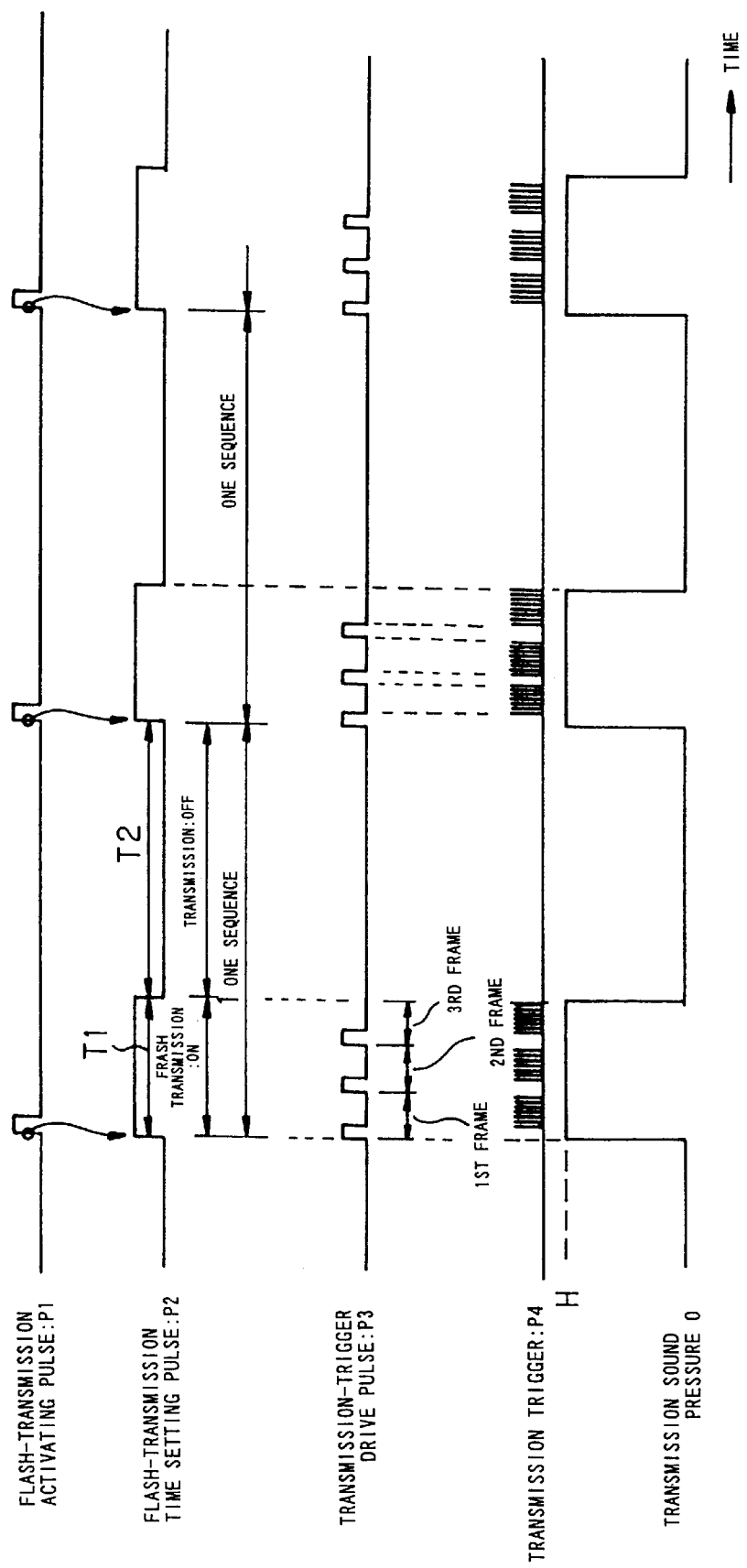
FIG. 3 shows a timing chart for explaining the operation of a transmission trigger controller.

FIG. 3 exemplifies a sequence showing on- and off-states of this transmission. In the transmission trigger controller 24, a flash-transmission time setting pulse P2 rises for a certain time T1 in synchronism with the rise of a flash-transmission activating pulse P1. The interval of this transmission time T1 is assigned to transmission (hereafter, referred to as flash transmission) for causing a flash echo phenomenon. For this certain time T1, three transmission-trigger drive pulses P3 commanding the acquisition of echo data for, for example, three frames in each of the CFM and B modes are generated at every certain interval. One pulse P3 is sent to the transmission trigger generator 21. After the elapse of the certain time T1, the flash-transmission time setting pulse P2 becomes an off-state for the next certain time T2. This interval T2 becomes a waiting interval in which the flash transmission is turned off. Thus controlling both the generation and stop intervals of the transmission trigger P4 makes it possible to readily obtain flash echo images effective in the CFM mode, as described later.

In this example, one period ranging from the beginning of the on-state of one flash transmission to that of the next flash transmission is called one sequence. An interval during which the flash echo phenomenon is caused is considered a few milliseconds to a few tens of milliseconds. Taking the lengths of such time into account, the transmission of an ultrasound pulse can normally be performed to obtain one to a few tens of frames at every certain time during the interval of the on-state of the flash transmission in each sequence.

With regard to the control of the on- or off-state of the transmission, there is an example in which an interval between both of the flash-transmission activating pulses P1 is set to equal ones or unequal ones, as shown in FIGS. 4(a) and (b). FIG. 4(a) shows one sequence where the pulse P1 always rises at a certain interval $\tau$, while FIG. 4(b) does the other sequence where the pulse P1 rises at each of unequal intervals $\tau 1, \tau 2, \tau 3 \ldots$.

Figure 4:
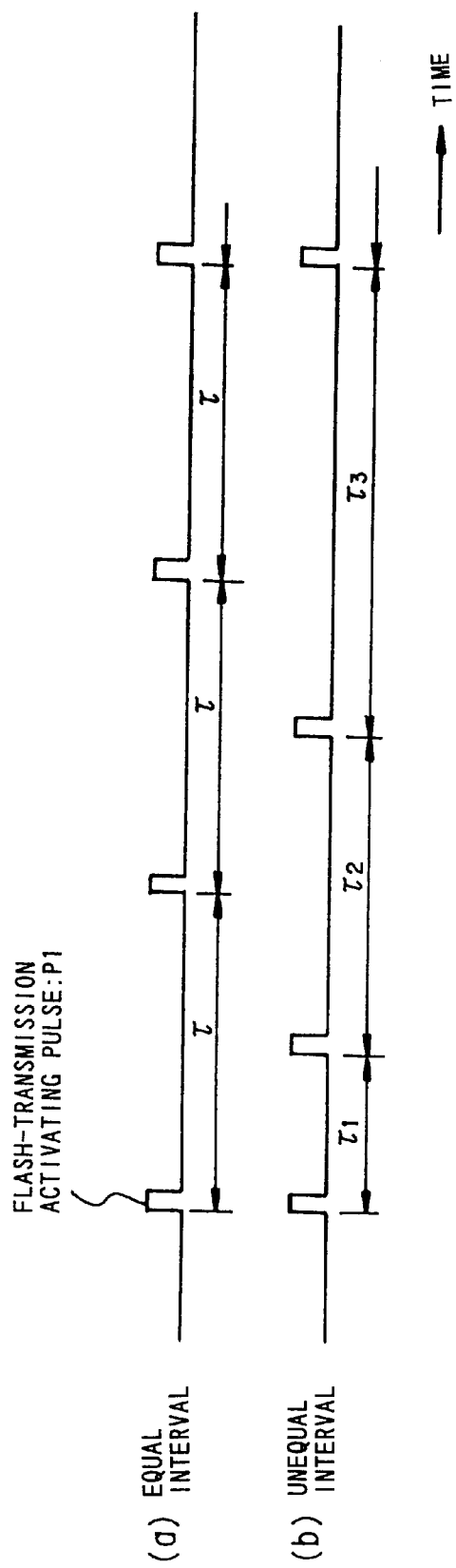
FIG. 4 is a timing chart explaining equal intervals and unequal intervals given to a flash-transmission activating pulse.
Figure 5:
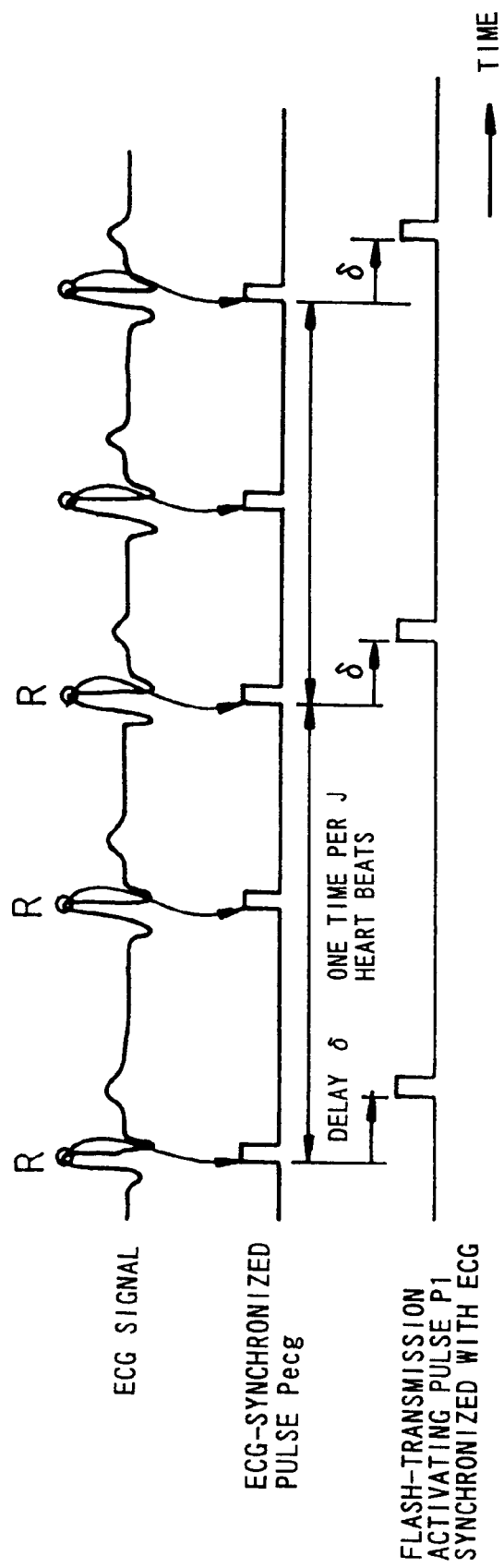
FIG. 5 is a timing chart for explaining an ECG synchronization technique.

As shown in FIG. 5, an ECG synchronized pulse $P_{ecg}$ is produced in synchronism with, for example, the R-wave of an ECG signal detected by the ECG meter 19. And a construction can be provided, in which the flash-transmission activating pulse P1 rises at an appropriate cardiac timing delayed by a given time $\delta$ from the pulse $P_{ecg}$ at every one or plural heartbeats. The sequences shown in FIGS. 4 and 5 are controlled in the transmission trigger controller 24.

Second, various amounts needed for the flash echo imaging can be designated by an operator by hand.

The number of scan frames for flash transmission can be designated by an operator through the operation panel 1 by hand. In addition, the value of the number can be changed according to a type of a contrast agent and an object for imaging. Although the interval of stopping the flash transmission is also can be changed on the basis of a type of a contrast agent and an object for imaging, it is in effect more convenient to make it possible that the period of one sequence for the on- and off-states of the flash transmission be designated by an operator through the operation panel 17, instead of controlling the interval of this stop, when considering ECG synchronization described later. The period of one sequence may be designed to a certain fixed value or values which differ sequence by sequence (refer to FIGS. 4(a) and (b)).

Further, the selection of the equal or unequal intervals for the flash transmission, setting lengths of those intervals, determining whether or not the ECG synchronization is performed, setting the delay time $\delta$ for the ECG synchronization, and setting a synchronized spacing of the ECG synchronization (a value of J heartbeats) may also be performed through the operation panel 17 by hand.

Figure 6:
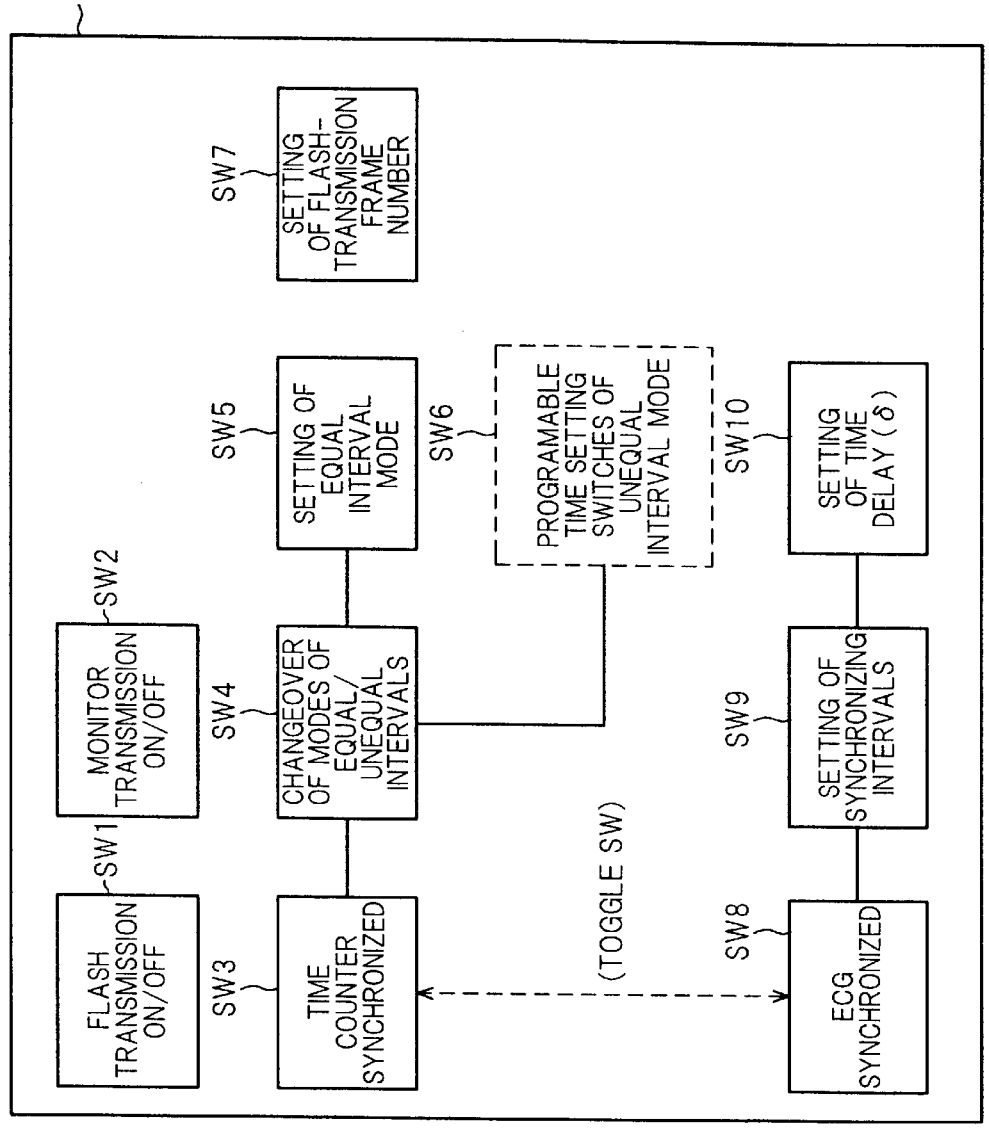
FIG. 6 illustrates one example of a group of switches equipped with an operation panel.

FIG. 6 shows an arrangement example of a group of switches operated by an operator and arranged on the operation panel 17. This arrangement example includes a flash transmission on/off switch SW1, monitor transmission on/off switch SW2, time counter synchronized switch SW3, equal/unequal interval changeover switch SW4, equal interval time setting switch SW5, unequal interval programmable time setting switch group SW6, flash-transmission frame number setting switch SW7, ECG synchronized switch SW8, synchronizing interval (a value J of heartbeats) setting switch SW9, and time delay $\delta$ setting switch SW10. Both of the time counter synchronized switch SW3 and the ECG synchronized switch SW8 are for setting a flash interval, which are structured into a toggle switch. Besides the above switches, the operation panel 17 has input devices, such as a keyboard and trackball, for allowing an operator to provide the controller 18 with necessary information.

A third characteristic is concerned with orders, for each mode; of the transmission trigger P4 outputted from the transmission trigger generator 21 to the pulse generator 22.

As imaging modes, this diagnostic ultrasound apparatus has B and CFM modes. When receiving a command issuing the start of flash transmission, the transmission trigger generator 21 has a configuration that it makes a transmission trigger P4 in the CFM mode precede that in the B mode at any time.

Every time receiving the transmission trigger drive pulse P3 shown in FIG. 3 from the transmission trigger controller 24, The transmission trigger generator 21 interprets it as being commanded to start the flash transmission by one frame for each of the B and CFM modes, and generates a transmission trigger P4. The transmission trigger P4 is generated as a set of triggers directed to both B and CFM modes, frame by frame. In this generation, the transmission trigger P4 in the CFM mode precedes that in the B mode. This precedence control is realized by logic circuits such as a counter or a CPU, both not shown, owned by the transmission trigger controller 21.

The reason why the precedence control is effective is as follows. If the transmission trigger P4 for the B mode is generated firstly, first transmitted is an ultrasound pulse in the B-mode is transmitted firstly. Thus a flash echo phenomenon is caused in the B-mode transmission. Because at least part or most of the microbubbles of the contrast agent have already been collapsed by the transmission, the CFM-mode transmission of an ultrasound pulse conducted immediately after the B-mode transmission generates only a feeble flash echo phenomenon. In other words, an echo signal (flash echo signal) associated with the flash echo phenomenon in the CFM mode is considerably lower in intensity or is nothing. To avoid this state, the CFM-mode transmission is given a priority.

FIG. 7(a) or (b) exemplifies a sequence in which the generation of a CFM-mode transmission trigger P4 precedes that of a B-mode transmission trigger P4. Of course, sequences other than this are possible to be performed. In the sequence in FIG. 7(a), for each raster, a CFM-mode transmission trigger is first generated, before a B-mode transmission trigger is generated. This combination is repeated for all the rasters to yield triggers used for one frame, and this repetition is further repeated by a specified number of frames. Alternatively, according to the sequence example in the FIG. 7(b), CFM-mode transmission triggers are first generated for one frame, then those for the B mode are generated for one frame. This combination is further repeated by a specified number of frames.

Hence, controlling the transmission triggers for the CFM mode such that they precede those for the B mode leads to giving priority to the CFM mode, raising sensitivity of the flash echo signal in the CFM mode.

Figure 8:
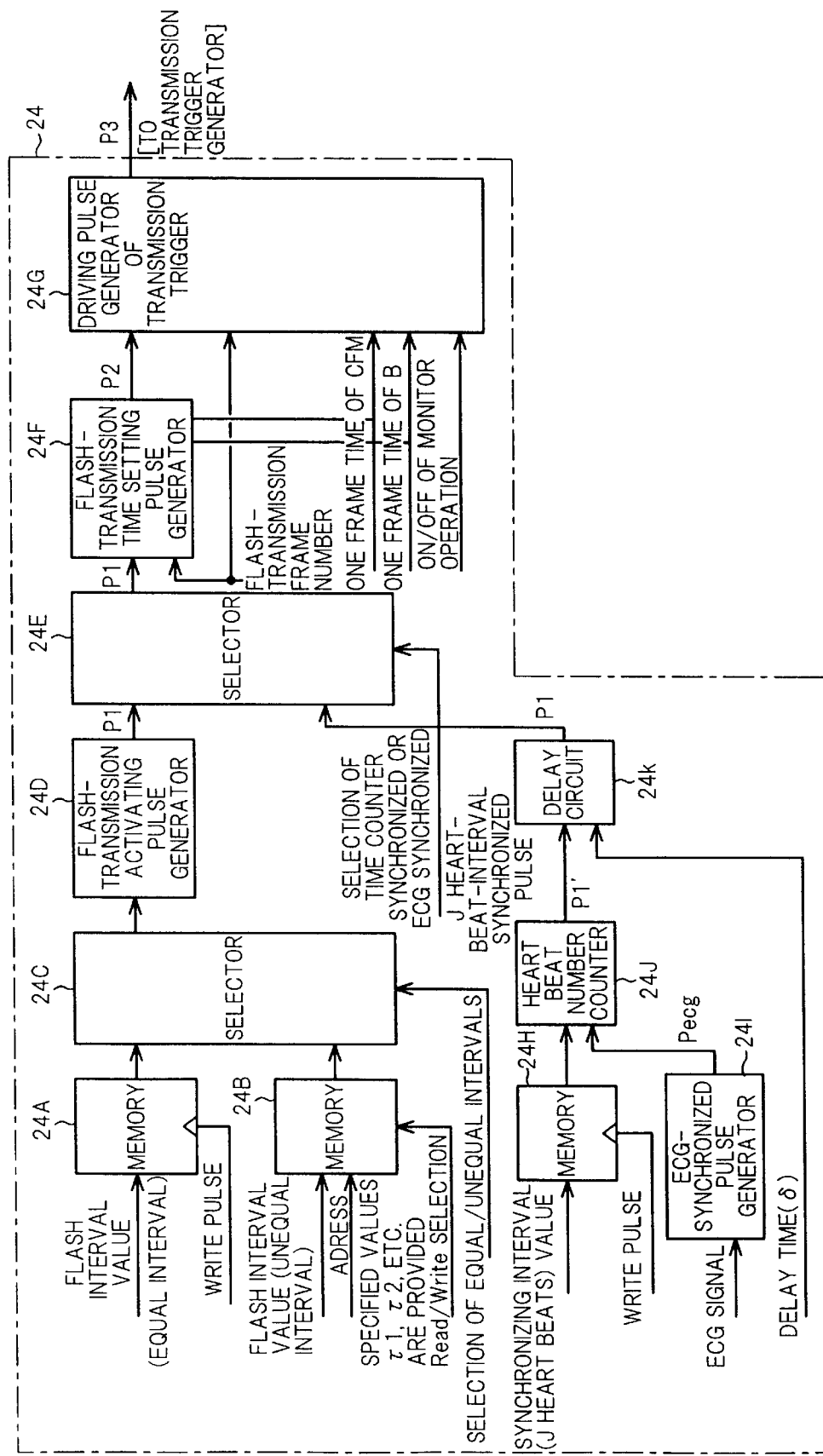
FIG. 8 is a detailed block diagram of the transmission trigger controller.

An example of configuration of the transmission trigger controller 24 is shown in FIG. 8. This controller 24 comprises two memories 24A and 24B and a selector 24C for setting a period of the flash transmission (i.e., corresponding to a period of one sequence). In one memory 24A, a flash-transmission equal interval value τ is written responsively to a writing pulse, the value being set by the equal interval time setting switch SW5. In the other memory 24B, unequal interval values τ1, τ2, . . . for flash transmission are written with their addresses specified, the values being set by unequal interval programmable time setting switch group SW6. The selector 24C changes over in answer to a signal from the equal/unequal interval changeover switch SW4, and selects an interval value read from either the equal-interval-side memory 24A or the unequal-interval-side memory 24B. This allows either mode of a flash-transmission equal or unequal interval to be selected (refer to FIG. 4), thus a selected interval value being outputted.

In this transmission trigger controller 24, there are further provided, at the output side of the selector 24C, a flash-transmission activating pulse generator 24D, selector 24E for selecting a synchronization technique, flash-transmission time setting pulse generator 24F, and transmission-trigger driving pulse generator 24G in this order.

The flash-transmission activating pulse generator 24D counts the interval value selectively outputted from the selector 24C by a time counter incorporated therein. And the generator generates a flash-transmission activating pulse P1 every time the count reaches a specified interval value, the generated pulse being sent to the selector 24E as an activating pulse based on the time counter synchronization technique.

In addition, the transmission trigger controller 24 further comprises, as circuitry for ECG synchronization, a memory 24H, ECG-synchronized pulse generator 24I, heartbeat number counter 24J, and delay circuit 24K. Of these, a synchronizing interval value (heartbeat value J: J is an integer of which value is one or more) set by the synchronizing interval (a value J of heartbeats) setting switch SW9 is written into the memory 24. The ECG-synchronized with pulse generator 24I receives an electrocardiograph (ECG) signal from the ECG meter 19 and generates the ECG-synchronized pulse $P_{ecg}$ synchronized the R-wave (refer to FIG. 5). The ECG-synchronized pulse $P_{ecg}$ is sent to the heartbeat number counter 24J. The heartbeat number counter 24J counts the number of the ECG-synchronized pulses $P_{ecg}$ to output a J heartbeat-interval synchronized pulse P1' when the count reaches the value J of the heartbeat read from the memory 24H. For example, in the case of the ECG synchronization technique shown in the foregoing FIG. 5, the synchronizing interval value=the heartbeat value J=two heartbeats is established, which means that the flash transmission becomes an on-state at a rate of one time per two heartbeats.

The J heartbeat-interval synchronized pulse P1' is given to the delay circuit 24K. Also given to this time 24K is a delay time δ designated through the time delay 6 setting switch SW10. Therefore the J heartbeat-interval synchronized pulse P1' undergoes a delay of time δ by the delay circuit 24K, then sent to the foregoing selector 24E as the flash-transmission activating pulse P1 based on the ECG synchronizing technique.

To this selector 24E, a setting signal from the time counter synchronized switch SW3 or ECG synchronized switch SW8 is given as a changeover control signal. Hence, depending on the type of the changeover control signal, the selector 24E selects either the flash-transmission activating pulse P1 outputted from the generator 24D based on the time counter synchronizing technique or the flash-transmission activating pulse P1 given via the delay circuit 24K based on the ECG synchronizing technique. This selected activating pulse P1 is sent to the flash-transmission time setting pulse generator 24F.

Given to this generator 24F is information about the number of frames for flash transmission sent from the flash-transmission frame number setting switch SW7, in addition to pieces of information about a necessary time for one frame of each of CFM and B modes later described. Hence, in synchronism with the selected flash-transmission activating pulse P1, the generator 24F generates a flash-transmission time setting pulse P2 (refer to FIG. 3) of which pulse length T1 agrees with the specified number of frames. This setting pulse P2 is sent to the final-stage transmission-trigger driving pulse generator 24G.

Supplied to this pulse generator 24G are times necessary for one frame of each of the CFM and B modes from the controller 18, an on/off signal for monitor operation from the monitor operation on/off switch SW2, and the number of frames for flash transmission above described. Among them, the information about the necessary time for one frame of each mode is decided by the CPU of the controller 18 through calculation based on data, such as a given pulse repetition time, the number of rasters for one frame, and others. By this, as shown in FIG. 3, the transmission-trigger driving pulse generator 24G generates the transmission-trigger drive pulse P3 at a desired rate only during the flash transmission time period in accordance with the designated number of frames. This drive pulse P3 is sent to the transmission trigger generator 21 as described before.

Moreover, circuitry of and after the transmission trigger generator will now be described. Every time one transmission-trigger drive pulse P3 is given, the transmission trigger generator 21 generates transmission triggers P4 consumed in one frame of each of the CFM or M modes, at a given pulse repetition time Tr (interval of transmitting an ultrasound wave) and in an order shown in FIG. 7(a) or (b), for example. The pulse generator 22 triggered by each transmission trigger P4 generates, trigger by trigger, a transmission pulse P5 having a given transmission frequency $f_0$ at the pulse repetition time Tr.

Every time when receiving the transmission pulse P5, the transmission circuit 23 gives this pulse P5 delay times different transducer by transducer and amplifies up to a desired voltage the delayed transmission pulse P5 of each transducer, thus drive pulses P6 being generated and applied to designated transducers of the probe 11. The number of transducers to be driven and the drive pulses P6 are determined such that a transmission aperture and a transmission voltage in the CFM mode become as large as possible within a regulation of safety to an object. An ultrasound pulse is therefore transmitted into the object by the prove 11.

The transmission frequency $f_0$ and/or the set voltage (corresponding to transmitted sound pressure) may be decided differently between the CFM and B modes. Normally, such a transmitting condition made to agree with each mode is given.

In the case of the CFM mode, the transmission circuit 23 repetitively provides the transducers with a pulse drive signal P6, N times (for example, 16 times), to which a delay time pattern composed of delay times, which are the same over the repetition, but different in time transducer by transducer. Thus the ultrasound pulse is repetitively transmitted N times in the same direction. For the next one sequence in which N-times of transmission are carried out, the delay time pattern for the pulse drive signal P6 is changed by small amounts of times, and the identical repetitive transmission is carried out. Repeating this permits a cross section to be scanned. In the case of the B mode, in the transmission circuit 23, a delay time pattern applied to the pulse drive signal P6 that is supplied to designated transducers is changed little by little at every time of transmission of a ultrasound pulse. These changes cause a cross section to be scanned.

The scanning in the CFM and B modes is executed for a designated number of frames, so that one time of flash transmission is completed. Then the transmission is stopped for waiting, and after a certain time of this waiting, the flash transmission is restarted, where the same sequence is repeated.

The ultrasound pulse forms a transmission beam due to the controlled transmission delay times while traveling within the object, and reflects partly at boundaries of different acoustic impedance values so as to produce echo signals. Part or all of each reflected echo is received by one or more transducers of the probe 11, and transformed into corresponding electric signals.

2.2. Configuration and Operation of Receiving System

On one hand, the receiver 13 connected with the probe 11 has a plurality of reception channels of signal processing systems coupled with each transducer of the probe. At the input side of each signal processing system of the reception channels, a pre-amplifier 31a (to 31n) is placed, while at the output side of each pre-amplifier 31a (to 31n), an A/D converter 32a (to 32n) and a digital type of receiving delay circuit 33a (to 33n) are placed in this order. Delay outputs from the receiving delay circuits 33a to 33n are added to each other by a digital type of adder 34.

Accordingly, the echo signal which has received by the probe 11 is taken in the receiver 13 every reception channel as a corresponding electric analog signal. This echo signal is then amplified every reception channel, before converted into a digital echo signal. This echo signal is in parallel delay-controlled every reception channel using delay times opposite in pattern to those in the transmission, and is added the other echo signals. This allows the receiver 13 to output an echo signal beam-formed with the same directivity as that for the transmission. This echo signal is then supplied to both B-mode and CFM-mode processors 14 and 15.

2.2.1. Configuration and Operation of B-mode Processor

The B-mode processor 14 consists of digital type of circuit groups handling digital signals and has a function of producing B-mode image data from echo signals supplied from the receiver 13.

This processor 14, although not shown in. detail, has a logarithm amplifier and an envelope detector. In this B-mode processor 14, an echo signal is first logarithm-amplified by the logarithm amplifier. And an output signal of the logarithm amplifier is subject to envelope-detection in the envelope detector. The detected signal is sent, as B-mode image data, to the display system 16.

By the way, it is sufficient that the B-mode images be produced with a fundamental wave, as explained by the conventional technique, but they may be produced with a harmonic wave, not limited to a particular type of image data composing the images.

2.2.2. Configuration and Operation of CFM-mode Processor

Further, the CFM-mode processor 15 is responsible for producing CFM-mode image data for the observation of blood flow dynamics in the CFM mode and is composed of digital type of circuit groups handling various kinds of processing in the state of digital signals.

The CFM-mode processor 15 has two signal processing systems which split at the input side, and into each system, a mixer 41a (41b), LPF 42a (42b), BPF 43a (43b), buffer memory 44a (44b), and MTI filter 45a(45b) are placed in this order. The output sides of the MTI filters 45a and 45b are coupled to the display system 16 through a calculator 46.

Of these configurations, the mixers 41a and 41b and the LPFs 42a and 42b constitute a quadrature phase detector to quadrature-phase-detect the echo data, so that Doppler data are extracted at each depth location associated with each time of transmission/reception. In this processor, there are provided a reference signal generator 47 generating a reference signal and a phase shifter 48 not merely giving an exact phase difference of 90 degrees to the reference signal but also providing the resulting signals to the mixers 41a and 41b. The reference signal has a frequency that is approximately the same as that of an echo signal to be detected. For instance, if a fundamental wave is detected, the reference signal is given the approximately same frequency as the fundamental wave of an ultrasound pulse to be transmitted, and if detecting a harmonic wave, the reference signal is given the approximately same frequency as the harmonic wave. As a result of it, a signal outputted from the receiver 13 is multiplied by the reference signals by the mixers 41a and 41b. This multiplication causes signals of which phases differ to each other by 90 degrees. The resultant signals are obliged to pass the respective LPFs 42a and 42b so that unnecessary RF components caused by the mixing are removed, Doppler data existing in the base band being extracted. That is, Doppler data are extracted from an acquired echo signal through the quadrature phase detection. This quadrature phase detection enables the separation of detection signals (separation of directions) between blood cells toward to the probe and away from the probe. The Doppler data are inputted into the BPFs (bandpass filters) 43a and 43b at every system.

The BPFs 43a and 43b are disposed to extract fundamental and/or harmonic waves from the Doppler data according to an object for imaging. The BPFs 43a and 43b provide a fourth characteristic configuration of the present invention.

Each of the BPFs 43a and 43b is able to pass only a fundamental wave, only a harmonic, or only fundamental and harmonic waves, with no processing exerted on them. The quadrature-phase-detected Doppler data includes four types of signals, which are a higher-intensity clutter signal as a fundamental wave corresponding to a transmission frequency, a higher-intensity signal from a contrast agent which has caused a flash echo phenomenon, a lower-intensity clutter signal considered owing to non-linearity of travel of an ultrasound wave in an object, which is a harmonic, and a still considerably higher-intensity signal although being lowered in intensity than the fundamental wave of the contrast agent which has caused the flash echo phenomenon.

Figure 9:
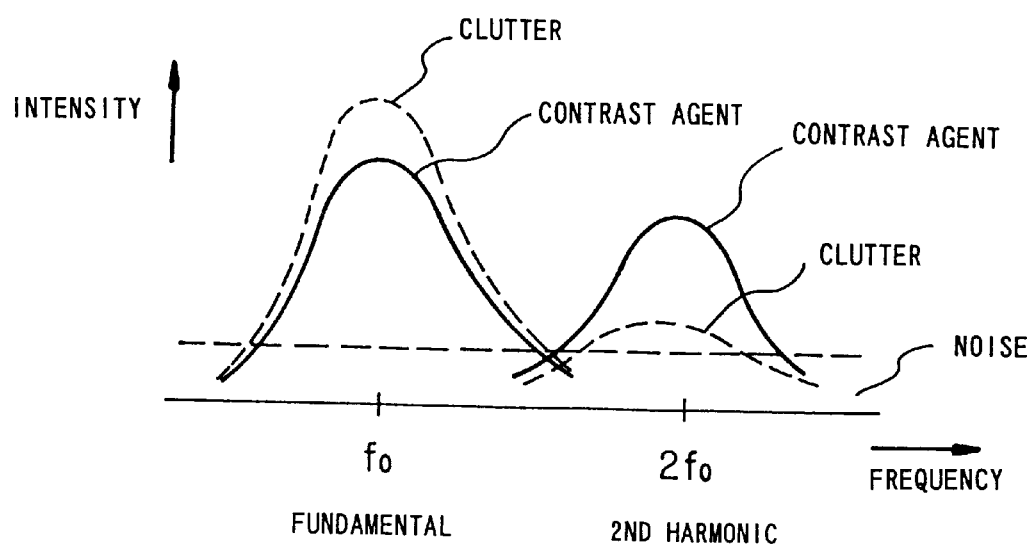
FIG. 9 is a frequency spectrum of both echo signals of a contrast agent and clutter components.

An example showing reception spectrums of such four types of waves (that is, spectrums of the output of the receiver 13) is pictorially shown in FIG. 9. This figure shows only a second harmonic having the highest intensity, which is adopted as one of the harmonics. Though the harmonics include a second harmonic, a third or more harmonic, and sub-harmonics, such as 1/2-th and 1/3-th one, the second one is normally the highest in intensity. Accordingly, for extracting a harmonic, it is better to extract only the second harmonic from an improved SIN point of view. Of course, in general, the harmonic is not confined to the second harmonic.

Additionally, it is acceptable that both fundamental and harmonic waves are made to pass the filter. But, a concept for realizing such an construction is the same as that for extracting the fundamental wave and an S/N in extracting only the fundamental wave is superior than in extracting both of the fundamental and harmonic waves. Thus, hereafter, both of the cases are not distinguished from each other, and they are unified by an expression of "extracting the fundamental wave."

On the basis of the above background, explained is extracting only a fundamental wave. Further, extracting a harmonic is explained in a fourth embodiment that will be referred later.

The advantages of extracting a fundamental wave originated from the flash echo phenomenon of a contrast agent are higher in intensity than harmonics and superior in detection sensitivity toward flows of blood. As described above, the fundamental wave contains the signal of a fundamental wave of higher intensity yielding from a contrast agent that has caused the flash echo phenomenon, and is the most advantageous to detection sensitivity. This higher sensitivity means that signals reflected by contrast agents residing at deeper positions within an object can be acquired in proportion to its highness. Namely, the deeper in penetration, the more deeply scanning can be performed. However, the fundamental wave also contains a clutter component of which intensity is higher. It is necessary to steadily eliminate the clutter component, because a signal component reflected by a contrast agent and the clutter component are mutually almost the same in intensity or the former is slightly weaker compared to the latter.

Figure 10:
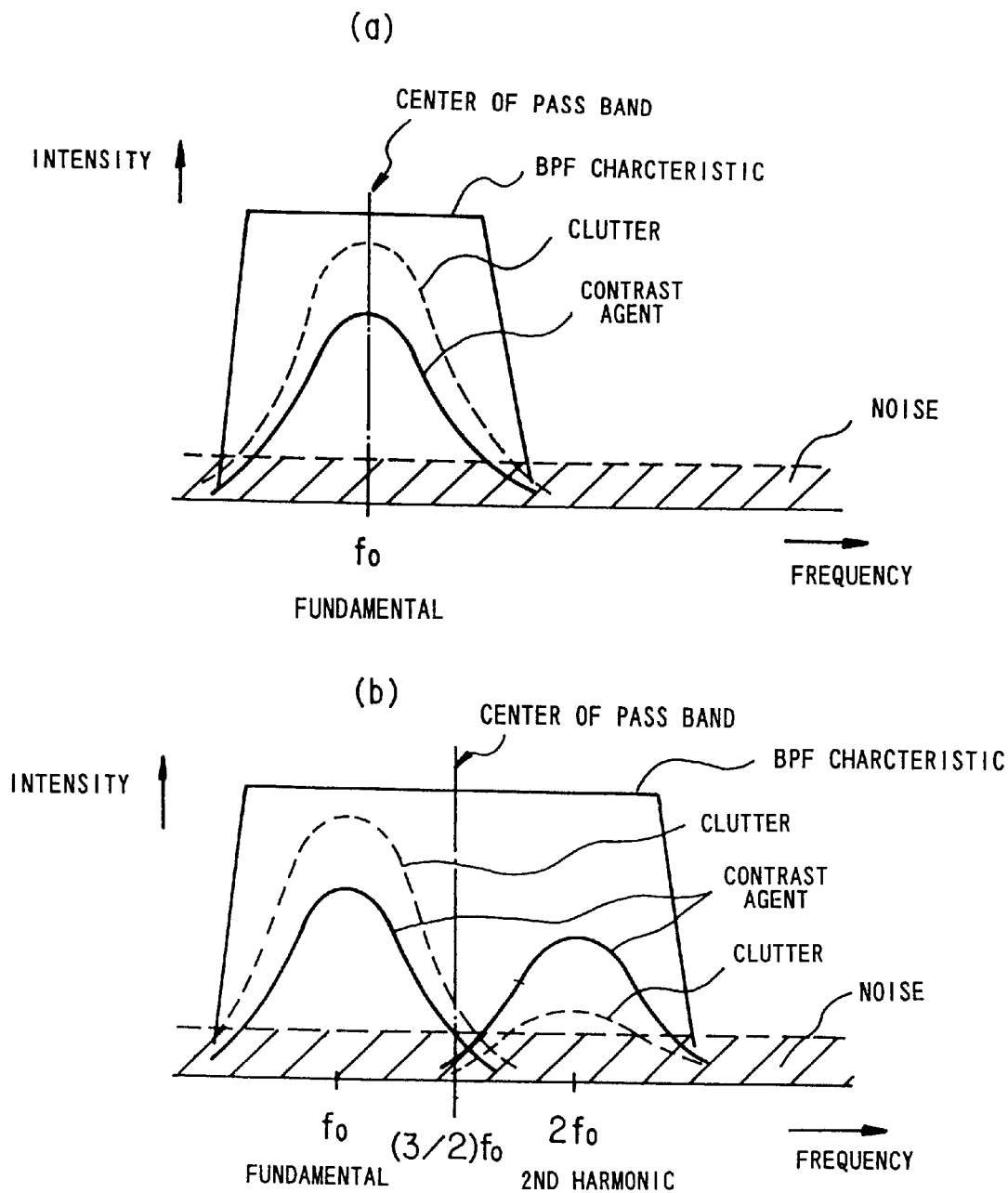
FIG. 10 is a frequency spectrum showing the relationship between the pass band of a BPF and a fundamental wave or the relationship between the pass band of a BPF and both fundamental and harmonic waves.
Figure 12:
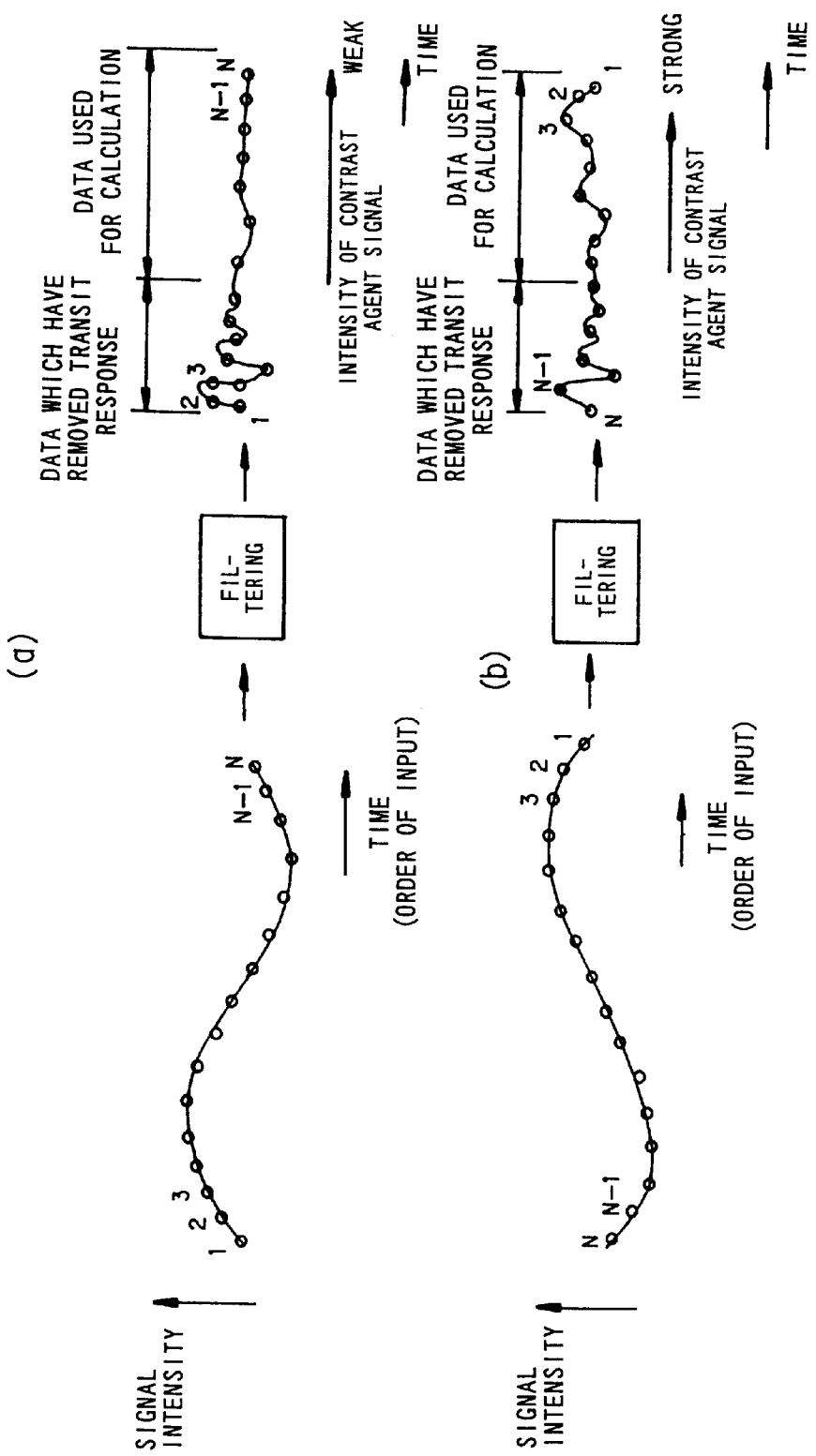
FIG. 12 illustrates transit responses of the MTI filter, initial data removal processing, and inverse reading processing.

To extract a fundamental component from Doppler data, as shown by the spectrums (spectrums before quadrature phase detection) in FIG. 10(a), the centers of the pass bands of the BPFs 43a and 43b are set to approximately a transmission frequency $f_0$, respectively, and the bandwidths thereof are determined in compliance with the band of an ultrasound pulse. Further, to simultaneously extract both fundamental and harmonic components from Doppler data, as illustrated by the spectrums in FIG. 10(b), the center of the pass band is shifted toward the harmonic side (for instance, to $1.5f_0$) such that the pass band is wide to include both fundamental and harmonic components. In practice, a frequency of the reference signal generator 47 in the quadrature phase detection circuit is set to approximately $f_0$ in the former case and to $1.5f_0$, for instance, in the latter case. Then quadrature phase detection is performed. With the center of the pass band being set to zero, the BPFs 43a and 43b each having a desired bandwidth at the band center zero are used to extract the fundamental wave or both of the fundamental and harmonic waves. From a hardware viewpoint, the BPFs 43a and 43b are respectively constructed into an LPF, but they functionally provide a BPF, respectively. In the following description, only a construction concerning the foregoing FIG. 10 will be described.

Therefore, using the fundamental wave leads to a flash echo image with higher penetration, because the fundamental wave has a flash echo signal having the highest sensitivity for detection.

The buffer memories 44a and 44b are disposed to temporarily store Doppler data for buffering, every signal system and read therefrom the time-sequential Doppler data, as a Doppler signal, yielding from each of the same positions of a cross section, during which reading the data at the same positions are such read that they are inversely inputted to each MTI filter 44a or 44b (inverse reading). This inverse reading, which constitutes a fifth characteristic of the present invention, makes it effective one measure against a transit response occurring in the MTI filters 45a and 45b described later, which is called "initial data removal," and increases the sensitivity of a flash echo signal.

To control this inverse reading, an input address counter 49 to control the data writing and an output address counter 50 to control the data reading are placed toward the buffer memories 44a and 44b.

In the case of the CFM mode, the same location of a cross section, i.e., the same raster is scanned a plurality of N times, and an echo signal acquired every time of scanning is quadrature-phase-detected. From Doppler data obtained by this detection, for example, a fundamental component is extracted by each BPF. Digital data of the fundamental component are sequentially stored in addresses of each of the buffer memories 44a and 44b specified by the input address counter 49. Accordingly, in terms of each raster, after the completion of N-times of scanning, two-dimensional Doppler data are stored in each buffer memory, where those data are composed of, as shown in FIG. 11(a), one dimension representing the number of times of transmission and reception of an ultrasound pulse and the other dimension representing the depth locations along each raster.

The necessity of the inverse reading and its background will now be described. The MTI filters 45a and 45b require reading the Doppler data and performing filtering to eliminate a clutter component therefrom. Conventionally, this was done in a manner that, with reading addresses changed by an output address counter, sequential N-pieces Doppler data obtained at the same location are read from each buffer memory and send to each MTI filter. In each of the MTI filters, clutter components are eliminated as described later, thus a signal component reflected from a contrast agent extracted alone.

In the filtering performed in the MTI filters, a transit response occurs in an earlier range of the filtered output waveform, as shown in FIG. 12(a). Therefore, when producing an image using all the N-piece data filtered, the image quality deteriorates noticeably due to the transit response. One conventional measure was that a few data that were early acquired and caused the transit response in the filtering were removed. And only remaining Doppler data that had no influence of the transit response were used to analyze both velocity and power, providing image data thereof. The processing that disposes of a few data first acquired is called "initial data removal."

However, a signal reflected from a contrast agent shows that Doppler data acquired temporarily earlier have higher signal intensity because microbubbles exist more densely before the signal intensity decays sequentially in time. To avoid the influence of the transit response, it is possible that a few data early acquired are disposed of. But this results in that the analysis of velocity and power is done by using only Doppler data composed of contrast agent signals having lower intensity. Thus signals reflected from a contrast agent are largely lowered in sensitivity.

To resolve this problem, the present invention employs a construction where, when N-piece time-sequential data acquired at each depth location along each raster are read from each of the buffer memories 44a and 44b, the order of the reading is inverted so as to first read data acquired temporarily last. This inverse reading allows Doppler data causing the transit response in the MTI filters 45a and 45b to be in a temporarily last part, in which signals reflected from a contrast agent are lessened in intensity or almost near to zero. Hence, as shown in FIG. 12(b), even if disposing of the Doppler data having caused a transit response, a train of Doppler data composed of signals intensely reflected from a contrast agent is left. Analyzing velocity and power using those remaining Doppler data increase its sensitivity and avoid drawbacks exerted on images due to the transit response.

The inverse reading from each of the buffer memories 44a and 44b is realized by making the output address counter 50 designate reading addresses in the following manner.

For the sake of an easier understanding, the description is limited to transmission and reception along a certain one-directional raster, but not necessarily limited to this one. In the foregoing data writing, the input address counter 49 counts up addresses in the order of, for example, 1, 2, 3, . . . , N·L, and in the buffer memory 44a (44b), Doppler data are stored at the designated addresses (refer to FIG. 11(a)). In other words, corresponding to the first time of transmission and reception, L-piece (for example L=1024) Doppler data, which is composed of 1, 2, . . . , L, are stored at the addresses of the depth locations along the raster. Next, corresponding to the second time of transmission and reception, L-piece Doppler data, which is composed of 1, 2, . . . , L, are stored at the addresses of the depth locations along the raster. Hereafter, the identical data storage to the above is sequentially performed at the addresses of the depth locations along each raster in the received order until the N-th transmission and reception is realized.

In contrast, for reading the Doppler data from the buffer memory 44a (44b), data at the same depth locations are read in turn from the shallowest depth location such that the order of transmission and reception becomes a sequence of N-th time, (N−1)-th time, . . . , the first time (refer to FIG. 11(b)). Namely, the output address counter 50 counts addresses in the order of:

$(N-1) \cdot L+1, (N-2) \cdot L+1, \ldots, (L+1), 1,$ $(N-1) \cdot L+2, (N-2) \cdot L+2, \ldots, (L+2), 2,$ $\ldots, \ldots, \ldots, \ldots, \ldots,$ $(N-1) \cdot L+J, (N-2) \cdot L+J, \ldots, (L+1), J,$ $\ldots, \ldots, \ldots, \ldots, \ldots,$ $N \cdot L, (N+1) \cdot L, \ldots, 2L, L$ This enables the reading of Doppler data in the temporal opposite order to the reception of echo signals, that is, to the writing thereof, from the N-th-time Doppler data to the first-time Doppler data, at each depth location.

Further, for every signal system, the MTI filters 45a and 45b receive inversely read Doppler signals sent from the buffer memories 44a and 44b, eliminate an unnecessary echo signal (clutter component) reflected at fixed reflectors such as the cardiac wall, and perform the foregoing "initial data removal." Thus, the clutter component is eliminated from the entire Doppler signal steadily and accurately, so that the reflected signal from the contrast agent is surely extracted.

As described above, the spectrum of a Doppler signal acquired from a contrast agent that caused the flash echo phenomenon is broad, but a clutter signal seldom causes Doppler shifts, so that it has a certain Doppler spectrum. Hence, the bandwidths of the MTI filters 45a and 45b are determined such that they make use of this difference in the Doppler spectrums to eliminate clutter signals.

By the MTI filters 45A and 45B, clutter components are eliminated, so that only signals reflected by a contrast agent are sent to the calculator 46. The calculator 46 has not only a device, for example, a self-correlator to infer information on dynamic modes of blood flows using Doppler data of real and imaginary parts but also an average velocity calculator, a disperse calculator, and a power calculator all of which use the correlated results. Accordingly, average velocities (Doppler frequencies) of the spectrum, amounts of dispersion of velocity distributions, power values of signals reflected from blood flows, and/or others are inferably calculated. These calculation results are sent to the display system 16 as image data in the CFM mode.

By the way, a filtered output from each of the MTI filters 45a an 45b is composed of data opposite in the acquisition order to that of the transmission and reception. That is, the phase of the Doppler shifts is turned in reverse and the signs representing the separation of directions of Doppler frequencies are also in reverse, providing an actual direction reversed. Accordingly, it is required to re-designate, that is, convert the signs so as to represent the right directions. This re-designation of the signs provides a sixth feature of the present invention, which is also conducted by the calculator.

For example, for the sake of an easier understanding, let assume that a Doppler frequency be composed of a single frequency $f_0$. If the Doppler data are in line in the same order as the transmission and reception, values of the a-channel are $xi = \cos(2\pi f_d iTR + \theta)$ and values of the b-channel are $yi = \sin(2\pi f_d iTr + \theta),$ where
i=P+1, P+2, . . . , N (in which the first P-piece data are removed, so the data range from P+1 to N.) and Tr: pule repetition time θ: initial phase.

Let assume i=1 and 2, but the generality is still maintained. If the data are in line in the same order as the transmission and reception, a detected Doppler frequency $f_{d,for}$ is expressed by:

$$f_{d,for} = (2\pi Tr)^{-1} \cdot \tan^{-1}[(x_1 y_2 - x_2 y_1)/(x_1 x_2 + y_1 y_2)]$$

$$= f_d$$

In contrast, if the data are in line in the reversed order to the transmission and reception, a detected Doppler frequency $f_{d,rev}$ is expressed by:

$$f_{d,rev} = (2\pi Tr)^{-1} \cdot \tan^{-1}[(x_2 y_1 - x_1 y_2)/(x_2 x_1 + y_2 y_1)]$$

$$= -(2\pi Tr)^{-1} \cdot \tan^{-1}[(x_1 y_2 - x_2 y_1)/(x_1 x_2 + y_1 y_2)]$$

$$= -f_d$$

Therefore, in the case that the data are in line in the reversed order to the transmission and reception, re-designating the signs of the calculated Doppler frequency provides Doppler frequencies having correct signs for directional separation. Thus, the average velocity calculator of the calculator 46 reverses the polarities of the signs (directions) of an obtained Doppler frequency.

Although a circuitry scale becomes slightly large, there is provided an alternative that has a similar advantage, in which buffer memories identical to the foregoing buffer memories 44a and 44b are placed at the output sides of the MTI filters 45a and 45b. And, through writing and reading to and from those buffer memories, the orders of data may reversed again to the original forward order of those data, the again-reversed data being inputted to the calculator 46.

2.2.3. Configuration and Operation of Display System

The velocity data or power data thus-calculated are sent to the display system 16. The display system 16 has a digital scan converter (DSC) 61 comprising two types of frame memories for the B and CFM modes and writing/reading control circuits, a color processor 62 coloring pixels, a D/A converter 63, a TV monitor for display. The digital-quantity data of images and velocities outputted from both B-mode processor 14 and CFM-mode processor 15 are written in each frame memory assigned to each processor of the DSC 61.

In the DSC 61, the data stored in both B-mode and CFM-mode frame memories are read with the standard TV technique, respectively. Concurrently with this reading, either one pixel of each positional-common pixel between both frame memories is selected, and one frame of image data in which a CFM-mode image (contrast agent, i.e., velocity data or power data of flows of blood) is superposed on a B-mode image (background image). The velocity data or power data are colored by the color processor 32, converted into analog signals by the D/A converter at every predetermined timing, and displayed on the TV monitor 34 as a CFM image on the flash echo imaging.

3. Entire Operation and Advantages

As described above, in this diagnostic ultrasound apparatus, the flash transmission is automatically on/off-controlled by the transmission trigger controller 24 at every certain interval. During the on-interval of the flash transmission, an ultrasound pulse is transmitted into an object. A contrast agent causes a flash echo phenomenon due to the irradiation of the ultrasound pulse, thereby emanating a signal component including higher-intensity fundamental and harmonic waves. In parallel, the ultrasound pulse is reflected at each boundary of acoustic impedance within the object. These echoes are mixed and received by all or part of the transducers of the probe.

On one hand, during the off-interval of the transmission, any particular processing concerning the transmission is not conducted, just waiting for a certain time.

The received signal is taken into the receiver 13. A digital-amount echo signal beam-formed in the receiver 13 is sent to both of the B-mode and CFM-mode processors 14 and 15. B-mode topographic image data are formed by the B-mode processor 14. In contrast, CFM-mode image data on the flash echo imaging, for example, blood-flow velocity mapping image data, are produced by the CFM-mode processor 15. Then, on the TV monitor 64 of the display system 16, a CFM-mode blood-flow velocity mapping color image is displayed on a white/black B-mode topographic image in a superposition mode.

Thus, with a contrast agent injected into an object, a CFM-mode image can be observed readily and accurately on flash echo imaging.

Particularly, as in the conventional apparatus, it is unnecessary to manually operate sophisticatedly, like temporarily stopping the transmission by manual-operating a freezing button in order to cause the flash echo phenomenon, then releasing this frozen state after a certain time. Hence, the flash transmission can be on/off-controllable in a steady and accurate manner. Each interval of the on- and off-states of this flash transmission is automatically calculated on given conditions. In addition, control is made such that the flash transmission of the CFM mode always precedes that of the other modes, with the result that a flash echo signal having a higher intensity can be received in the CFM mode.

Further, it is enough for an operator to give a desired flash transmitting condition and a scanning condition through an operation panel. Of course, those conditions can easily be changed via the operation panel, while the apparatus is able to automatically trace those changed conditions. If an operator desires, an ECG synchronization technique can be used together in the apparatus.

Further, in the signal processing in the CFM mode, the BPFs allows fundamental and/or harmonic components resulting from the flash echo phenomenon of a contrast agent to be extracted appropriately from echo data that have experienced the quadrature phase detection. It can therefore be determined that which component be extracted according to characteristics of detection sensitivity and others in the flash echo imaging.

Still, the MTI filters make it possible to eliminate a clutter component from fundamental and/or harmonic components, thus steadily extracting only Doppler data originating from blood flows. In this filtering, conversion is made such that an input order of a train of Doppler data to the MTI filters become the opposite sequence to a detected order thereof (inverse reading). Thus, Doppler data in an early stage that will be influenced by a filtering transit response in the MTI filters are positively assigned to data that have received weakly a flash echo phenomenon. Namely, data eliminated by processing called "initial data removal" are Doppler data that have received weakly the flash echo phenomenon. The influences of the transit response can therefore be avoided steadily, while Doppler data that have experienced strongly the flash echo phenomenon are left for a high-accuracy velocity analysis.

Still, data that experienced velocity analysis by the calculator are also subjected to the re-designation of their signs conducted therein. Therefore, performing the above inverse reading leads to correct separation of directions of blood flows.

In consequence, this diagnostic ultrasound apparatus can provide a high practicality particularly in the actual field of clinics and a higher-sensitively detection that a variety of kinds of processing are suitable for detection and processing of an enhanced signal caused by the flash echo phenomenon. Thus a diagnostic ultrasound apparatus that is superior in both maneuverability and practicability, high in diagnostic performance, and capable of the flash echo imaging in the CFM mode is provided.

In the foregoing configuration, in the CFM mode processor, the BPFs are placed into the two channels a and b, respectively, after the quadrature phase detectors. When adopting such BPFs' disposal positions, the BPFs can be designed in an easier way.

Moreover, in this embodiment, the diagnostic ultrasound apparatus employs the receiving and processing systems 13 to 15 composed into a digital type of circuit configuration in which the A/D converters are placed immediately after the receiving amplifiers, respectively. Thanks to this digitalization, in addition to stabilized circuit operations, improvement of performances of the receiver and processing system circuits and diversity of processing can be enhanced.

Additionally, this embodiment has explained a mode in which a CFM image is displayed on a topographic image, but the present invention is not always limited to such a display mode.

Third Embodiment

Figure 13:
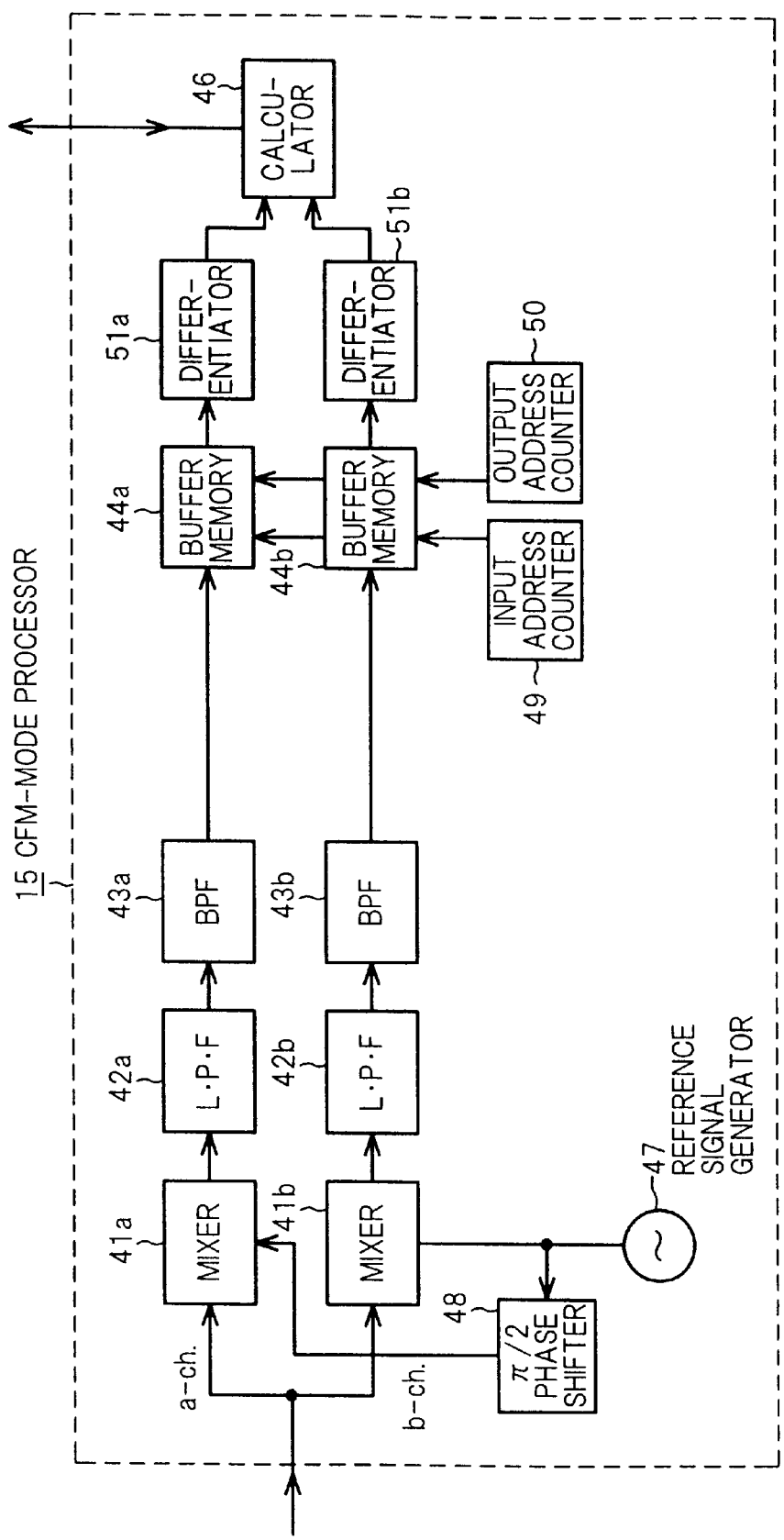
FIG. 13 is a block diagram showing a CFM-mode processor of the diagnostic ultrasound apparatus according to a third embodiment of the present invention.

Referring to FIG. 13, a third embodiment of the present invention will now be described. In this embodiment or embodiments described later, the identical or similar constituents to those in the second embodiment are given the same references to omit or simplify their explanations.

A diagnostic ultrasound apparatus according to this embodiment relates to another configuration to eliminate a clutter component, which is incorporated in the foregoing CFM processor 15. Practically, the apparatus features the use of a differentiator based on a difference technique, instead of the foregoing MTI filters.

FIG. 13 shows a digital type of CFM-mode processor 15. This processor 15 has differentiators 51a and 51b placed into each signal system after the buffer memories 44a and 44b. The differentiators 51a and 51b are configured so that their difference outputs are respectively supplied to the calculator 46. The other configurations are identical to those written in FIG. 2.

The operation of the differentiators or their surroundings will now be described. With addresses changed by the output address counter 50, N-piece of Doppler data acquired at the same depth location are read from the buffer memories 44a and 44b, respectively. In this case, an order of this reading complies with an order of transmission and reception at the same depth location. Adjoining ones of the thus-read Doppler data are differentiated by each of the differentiators 51a and 51b.

Specifically, when assuming that Doppler data to be inputted into the differentiator 51a in the a-channel is $i_1$, $i_2$, $i_3$ and $i_4$, its outputs are $(i_2-i_1)$, $(i_3-i_2)$, and $(i_4-i_3)$. The identical differentiation is applied to the b-channel. Because the clutter is almost stationary, a clutter component of the adjoining Doppler data is approximately the same in value, which is eliminated by the differentiation. In contrast, a flash echo signal has a wide-band (broad) Doppler frequency, so it is considered that the signal has a disturbed temporal waveform, which is not eliminated by the above differentiation, resulting in its passing.

Accordingly, this differentiation eliminates a clutter component and extracts a flash echo signal. In particular, this differentiation will not cause a transit response phenomenon by the calculation. Hence, it is not necessary that the "initial data removal" employed as a countermeasure against the transit response phenomenon described in the second embodiment. The inverse reading from the buffer memories are therefore unnecessary. On the other hand, Doppler data acquired before, which are derived a flash echo signal higher in intensity, are used for velocity analysis without any particular processing, securing a higher sensitivity in velocity detection.

Fourth Embodiment

Figure 14:
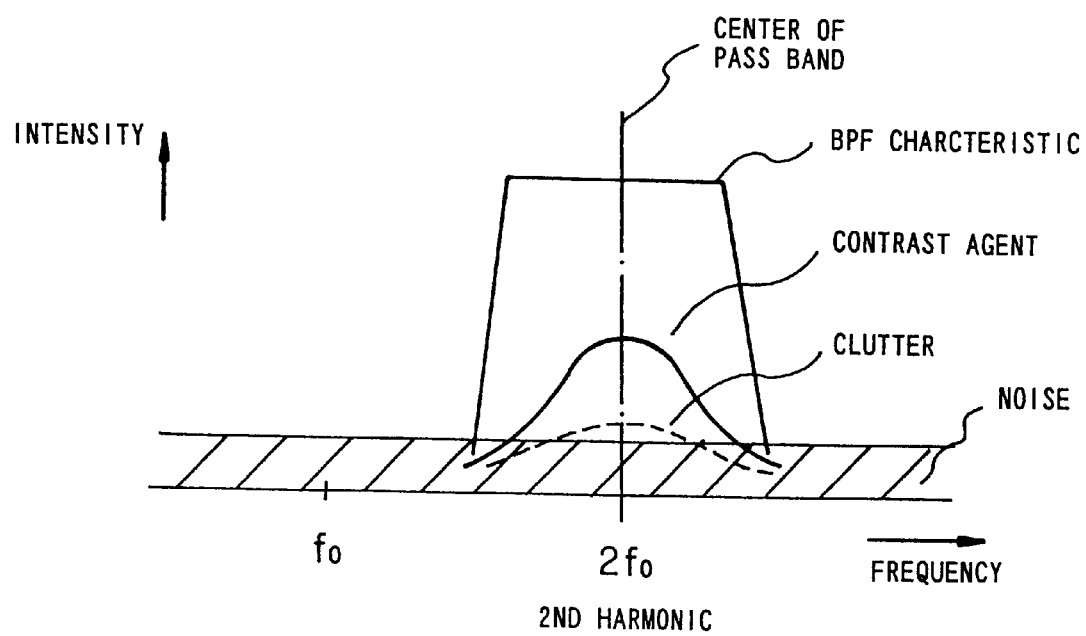
FIG. 14 is a frequency spectrum showing the relationship between the pass band of a BPF and a second harmonic in a diagnostic ultrasound apparatus according to a fourth embodiment of the present invention.

Referring to FIG. 14, a fourth embodiment of the present invention will be described. A diagnostic ultrasound apparatus of this embodiment has a feature of extracting a harmonic caused by the flash echo phenomenon of a contrast agent, using the BPFs arranged in the CFM processor.

An advantage of extracting a harmonic is that the harmonic processes a capability to eliminate a certain artifact, differently from the case that a fundamental wave is extracted. Of the artifacts, the strongest one is an echo from the organic parenchyma, that is, a clutter component, which is acquired by the main-lobe of an acoustic field. But depending on positions to be examined, there exists another artifact that has a higher Doppler frequency, though weaker in intensity, like seen in acquiring the motion of the cardiac muscle by side lobes of the acoustic field. If using a fundamental wave, the Doppler frequency of a clutter component is approximately zero, so that the clutter component can be eliminated by the MTI filters. But, the above latter-described artifact cannot be eliminated by the MTI filters, resulting in that the artifact is on an image.

Under these circumstances, the extraction of a harmonic is more effective. Namely, due to the fact that the above latter-described artifact is weak in intensity and has no harmonic, such artifact can be disregarded by extracting the harmonic. A clutter component is also composed of essentially a fundamental component, with the result that such artifact can be almost disregarded by extracting the harmonic. In contrast, an echo signal from a contrast agent includes a harmonic component of which intensity is high. Thus extracting a harmonic leads to the extraction of the contrast agent. In other words, the extraction of a harmonic results in the elimination of an artifact that has not been eliminated by the MTI filters or the differentiators.

Practically, as shown in FIG. 14, a harmonic can be extracted by making the center of the pass band of each BPF 43a (43b) coincide with double a transmission frequency $f_0$ and determining the bandwidth of each BPF depending on the band of an ultrasound pulse. The harmonic thus extracted is temporarily stored in each buffer memory 44a (44b), and then it undergoes the basically identical processing to that for a fundamental wave.

The artifact and most of the clutter component are eliminated by each BPF 43a (43b). Therefore, even if Doppler data are inputted directly to the calculator to obtain velocity data, without the foregoing MTI filters or differentiators, it is possible to sufficiently observe signals resulting from a contrast agent.

However, there actually exits a harmonic component of the clutter component, though its intensity is fairly low. The foregoing MTI filters 45a and 45b or differentiators 51a and 51b can therefore be used together to further eliminate a remaining clutter component. This obtains CFM images from which the artifact is more steadily eliminated. Accordingly, even when the pass bands of the BPFs 43a and 43b are adjusted for the harmonic extraction, it is preferred that the MTI filters or differentiators are used together.

By the way, when extracting a second harmonic as the harmonic, a Doppler frequency does not become a Doppler frequency transmitted and received at $f_0$ but equal a Doppler frequency transmitted and received at $2f_0$. (Refer to, for example, a literature "Japanese Journal of Medical Ultrasonics, Vol.21, Supplement 1; May 1995; 65–211.") In this description, for the sake of an easier understanding, a premise is made such that a reference frequency is $f_0$ equal to a transmission frequency, but the generality is still maintained. Accordingly it is necessary to correct a difference between those frequencies in the calculator 46. A Doppler velocity $v_d$ is calculated by the calculator 46 based on an expression of:

$$v_d = f_d \cdot (1/(2f_0)) \cdot (c/2) \cdot (1/\cos\theta),$$

instead of an expression used for extracting a fundamental wave, that is,:

$$v_d = f_d \cdot (1/f_0) \cdot (c/2) \cdot (1/\cos\theta),$$

where $f_d$: Doppler frequency, c : sound velocity, and $\theta$: angle made between a flow and an ultrasound beam.

Thus, in the CFM-mode processor, a harmonic component is extracted by the BPFs, and a CFM image is produced based on this component. For this production, a capability to eliminate artifacts is kept high, so artifacts can be eliminated at diagnostic regions where it was impossible to eliminate them in the past. Hence, CFM images having a higher image quality and a higher diagnostic performance can be provided on flash echo imaging.

As a modification, there is provided a construction where one mode for producing images using a fundamental wave emanated from a contrast agent, which was described in the second embodiment, and the other mode for producing images using a harmonic emanated from a contrast agent, which was described in this embodiment, are selectively changed over and used according to situations.

Fifth Embodiment

Figure 15:
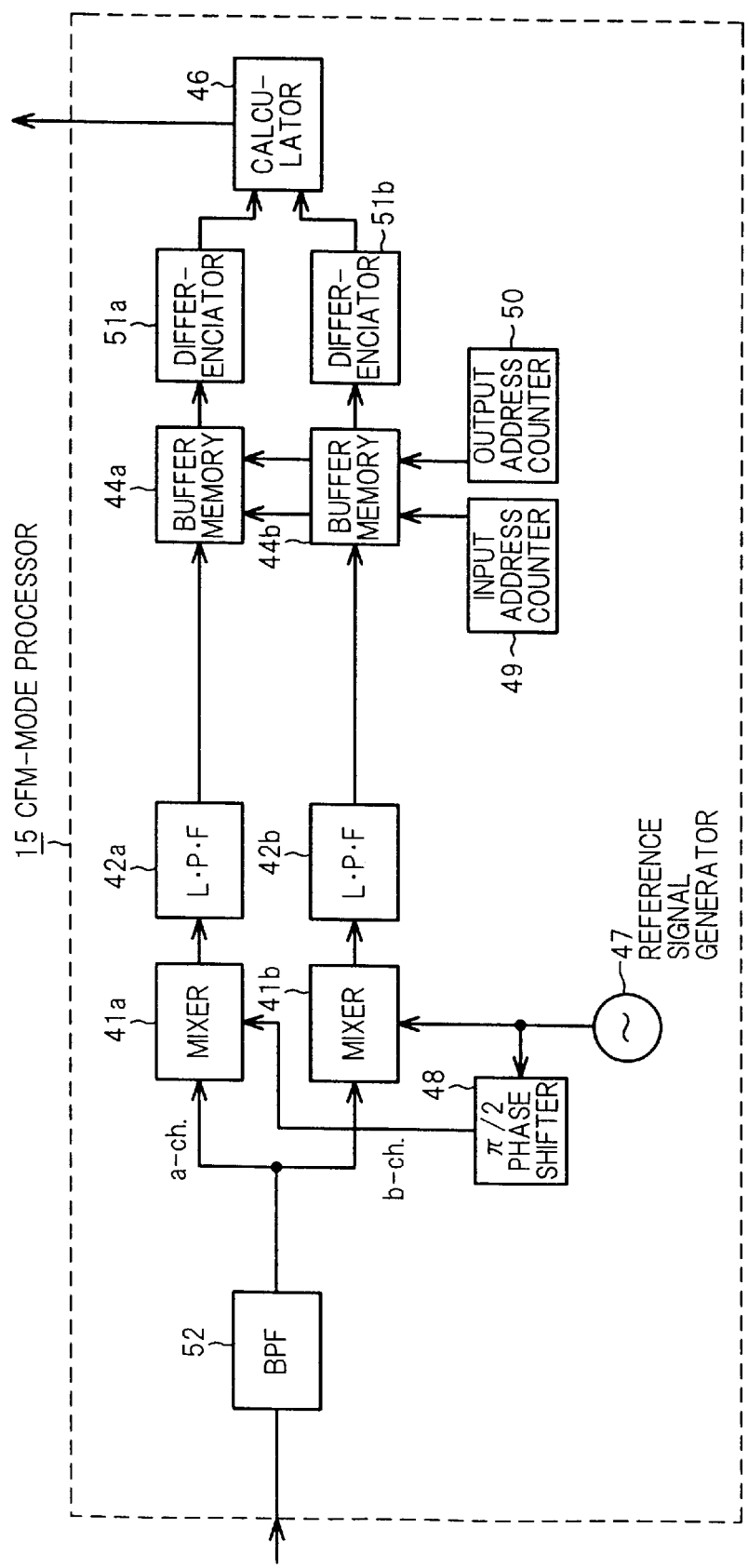
FIG. 15 is a block diagram showing a CFM-mode processor of a diagnostic ultrasound apparatus according to a fifth embodiment of the present invention.

Referring to FIG. 15, a fifth embodiment of the present invention will now be described. This embodiment is characteristic of positions at which the foregoing BPFs are located.

As shown in FIG. 15, in the CFM-mode processor 15, a BPF is located at a different position from the configuration of FIG. 13. Specifically, the position of the BPF is changed from the output side of the a- and b-channel detectors to the input side thereof, and the single BPF 52 is used in common for both channels.

This makes the BPF 52 extract from an echo signal sent from the receiver only a fundamental wave, a harmonic wave, or fundamental plus harmonic waves resulting from the flash echo phenomenon of a contact agent, and send the extracted signal to the preceding quadrature phase detector where a Doppler signal is extracted.

In this construction, there is an advantage that a single BPF 52 is enough.

Alternatively, as to the location of the BPF, the construction of FIG. 14 can preferably be applied to the CFM-mode processor of FIG. 2.

Sixth Embodiment

Figure 16:
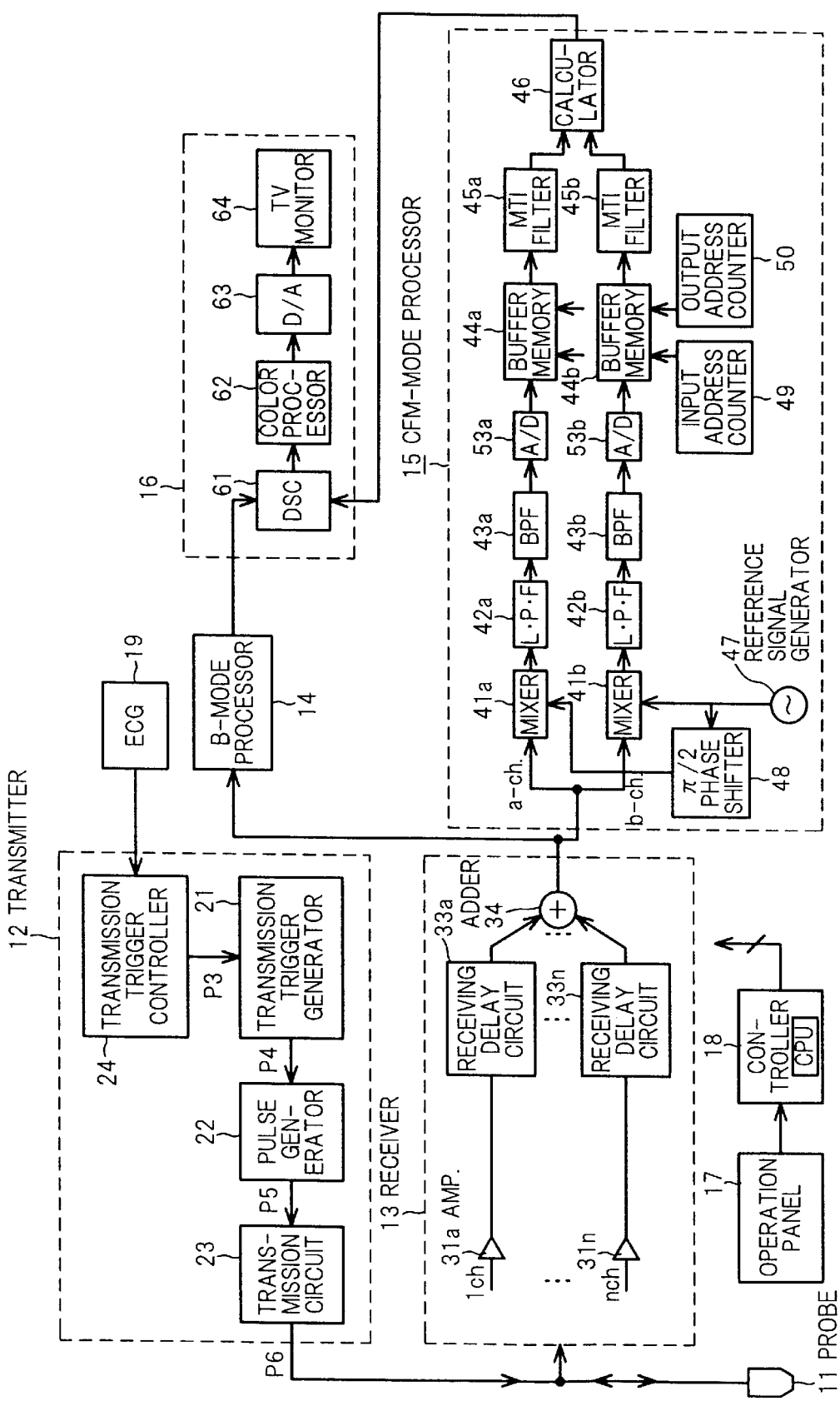
FIG. 16 shows a block diagram of a diagnostic ultrasound apparatus in accordance with a sixth embodiment of the present invention.

Referring to FIG. 16, a sixth embodiment of the present invention will now be described. This embodiment provides analog type of circuitry, instead of the receiver and the B-mode and CFM-mode processors formed into digital types.

In a diagnostic ultrasound apparatus shown in FIG. 16, the amplifier 31a (to 31n) placed in each reception channel of the receiver 13 is directly coupled with the receiving delay circuit 33a (to 33n). In place of this connection, in the CFM-mode processor 15, an A/D converter 53a (53b) is disposed between the BPF 43a (43b) and the buffer memory 44a (44b) in each of the two a- and b-channels. Accordingly, digital signals are handled from the stage of writing data into the buffer memories.

This construction is advantageous in that only two A/D converters are enough. Whether adopting the digital type shown in FIG. 2 or adopting the analog type shown in FIG. 16 can be decided on mutual comparisons of manufacturing cost, the performances of signal processing, and others.

Seventh Embodiment

Referring to FIGS. 17 to 20, a seventh embodiment of the present invention will now be described. A diagnostic ultrasound apparatus of this embodiment is characteristic of performing transmission (hereafter called monitor transmission) for obtaining monitor images, of which condition is differently set from the flash transmission, in order to prevent positional shifts between the probe and an object, which might occur in a state with no flash transmission (that is, an interval waiting for the recharge of microbubbles into a diagnostic region (raster region)).

In the case of the foregoing embodiments, since no image can be obtained during an off-state of the flash transmission, the positional determination of a region to be examined is impossible by the observation of the screen. As a result, if the probe position is relatively sifted on an object, it is difficult to become aware of such positional shifts during the flash transmission "off."

Figure 17:
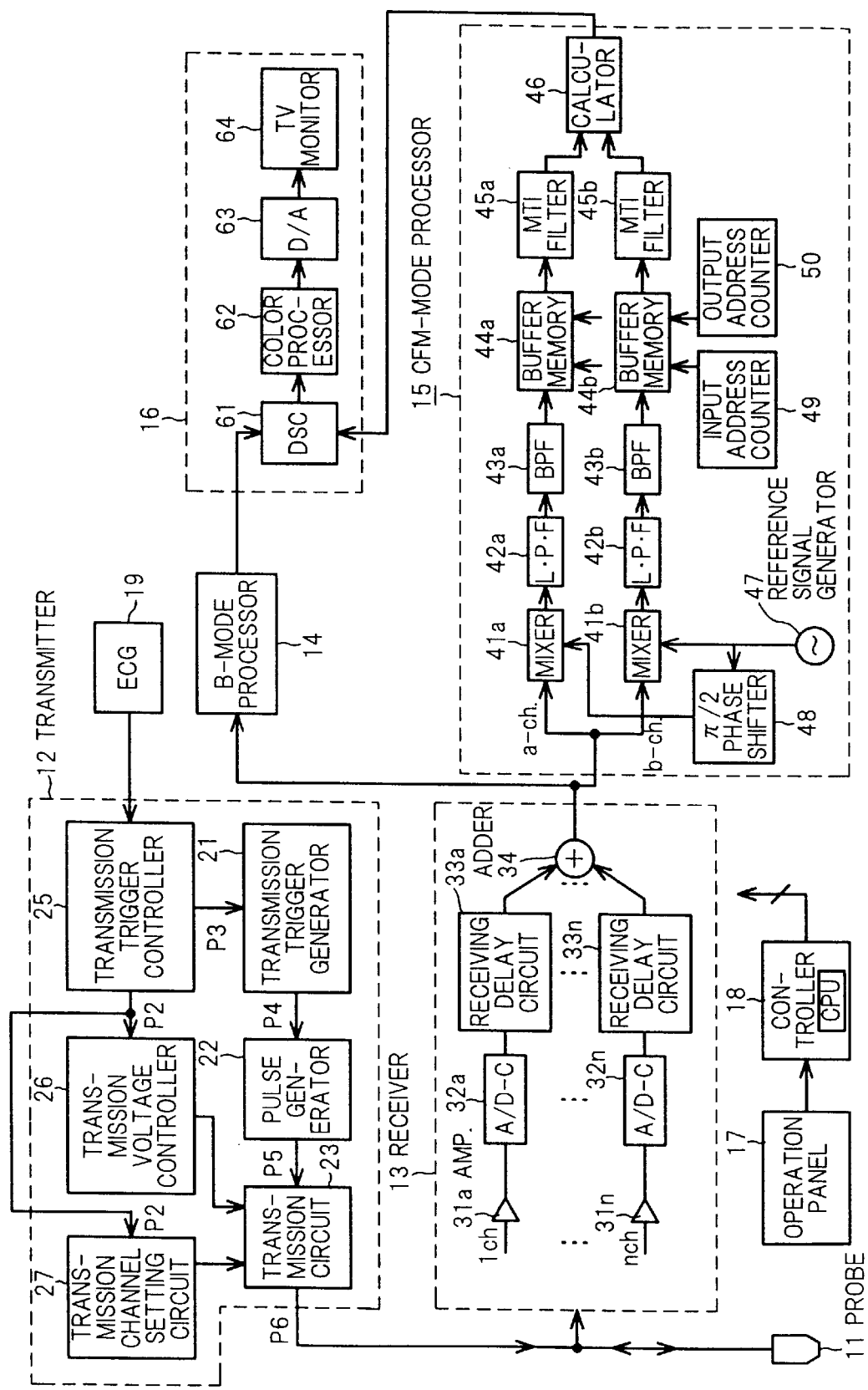
FIG. 17 shows a block diagram of a diagnostic ultrasound apparatus in accordance with a seventh embodiment of the present invention.
Figure 18:
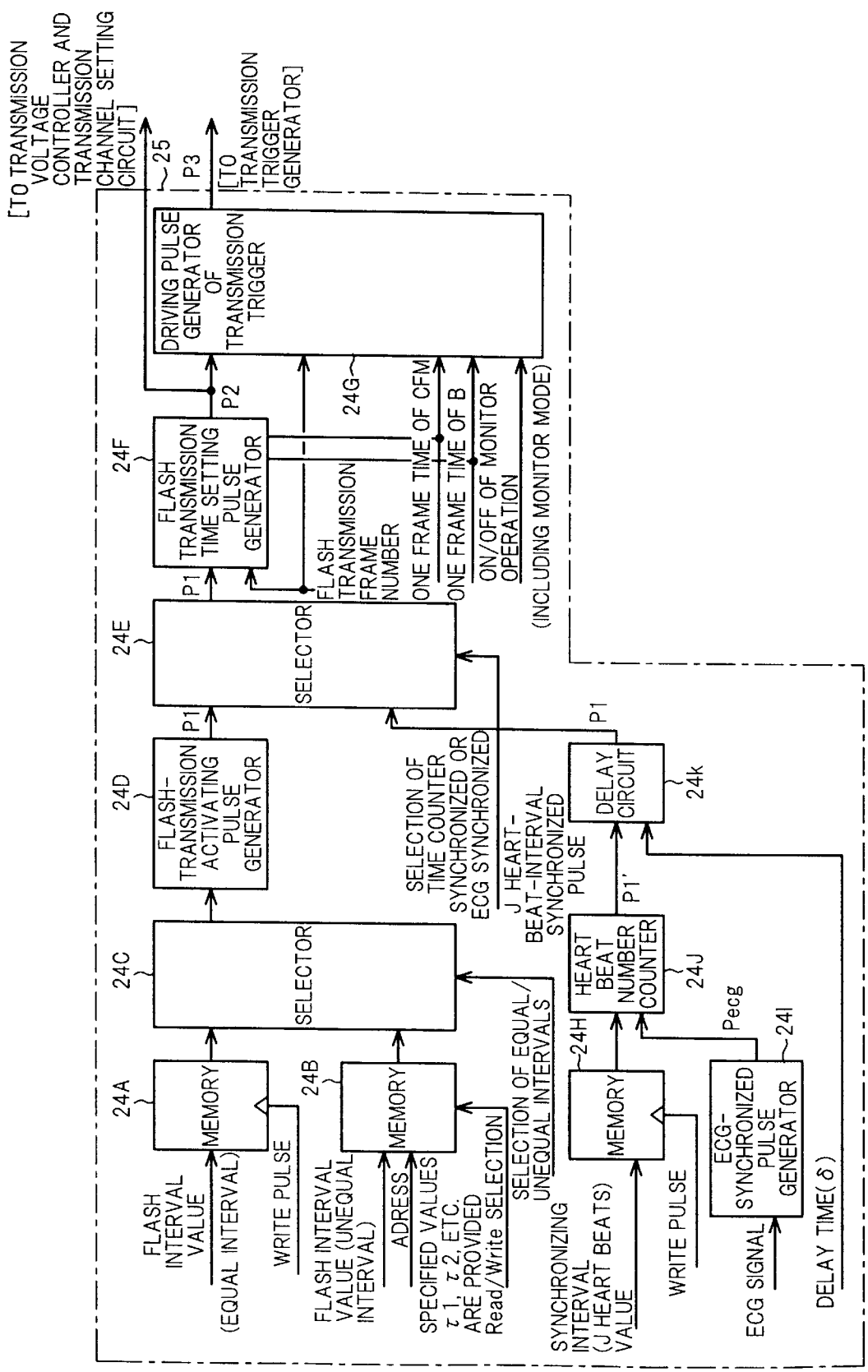
FIG. 18 depicts a block diagram of the configuration of a transmission trigger controller.

In order to overcome such a situation and enhance the practicality of the diagnostic ultrasound apparatus of the present invention, this embodiment provides a diagnostic ultrasound apparatus shown in FIGS. 17 and 18.

FIG. 17 shows the entire configuration of this diagnostic ultrasound apparatus, which corresponds to the foregoing configuration of FIG. 2. As depicted in FIG. 17, this apparatus is provided with a transmitter 12 that performs the foregoing monitor transmission. This transmitter 12 comprises, in addition to the transmission trigger generator 21, pulse generator 22, and transmission circuit 23, a transmission trigger controller 25 inherent to this embodiment, a transmission voltage controller 26, and a transmission channel setting circuit 27. As will be described later, either the transmission voltage controller 26 or the transmission channel setting circuit 27 could be used alone.

FIG. 18 exemplifies a practical configuration of the transmission trigger controller 25. This controller 25 has a configuration in which the generation of the transmission triggers are controlled for every transmission mode (namely, flash transmission or monitor transmission) toward the transmission trigger generator 21, like the foregoing embodiment, during which processes pulses generated on the control are also used to control both transmission voltage controller 26 and transmission channel setting circuit 27.

The transmission trigger controller 25 is configured based on the circuitry of FIG. 8 and has a functionally upgraded transmission trigger driving pulse generator 24G. To this generator 24G, an on/off signal for the monitor transmission is sent from the monitor transmission on/off switch SW2 of the operation panel 17. This on/off signal contains bits of information about a monitor mode under which the monitor transmission is performed in the B-mode or CFM-mode technique.

Figure 19:
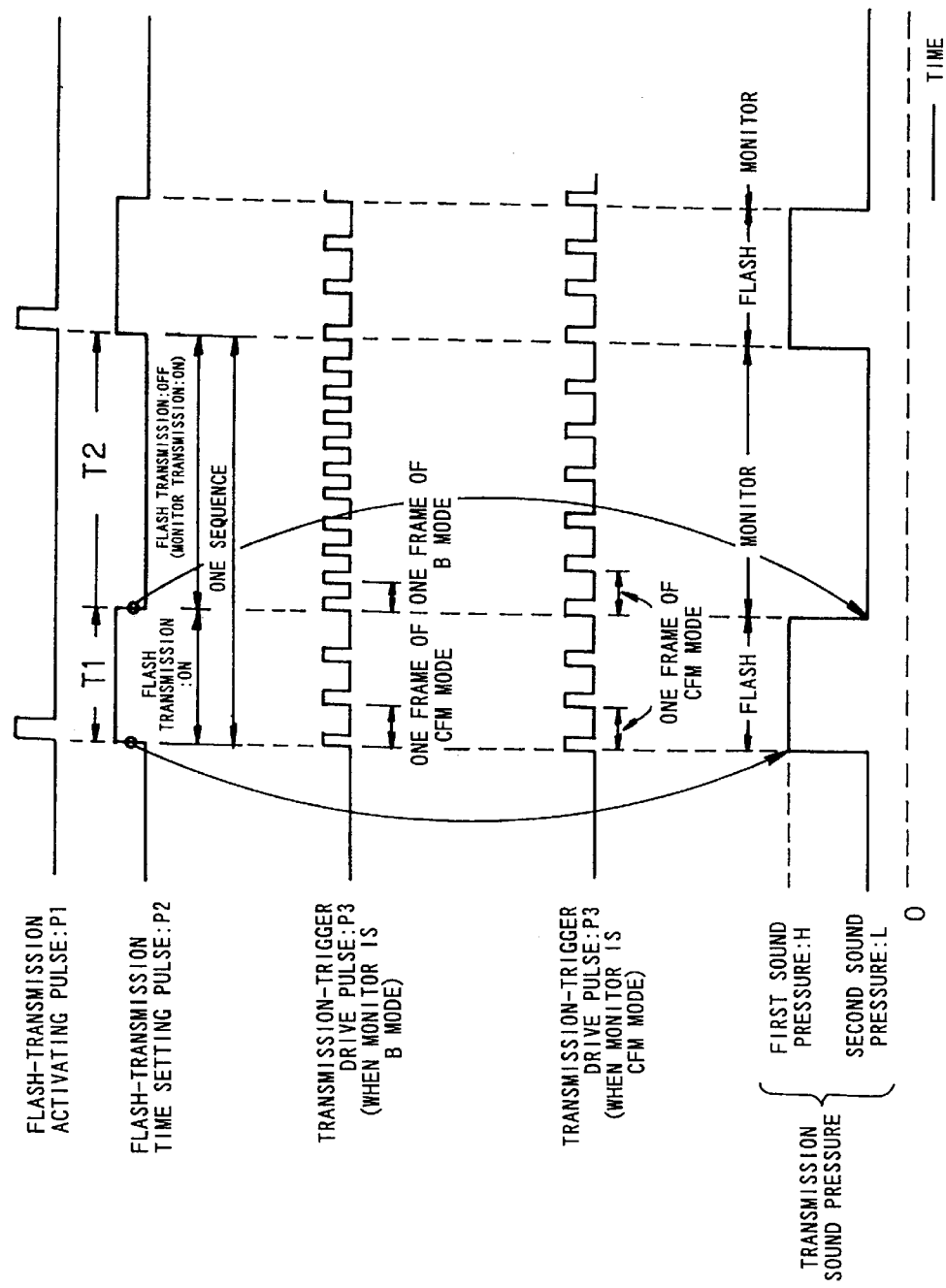
FIG. 19 is a timing chart for illustrating the operation of the transmission trigger controller.
Figure 20:
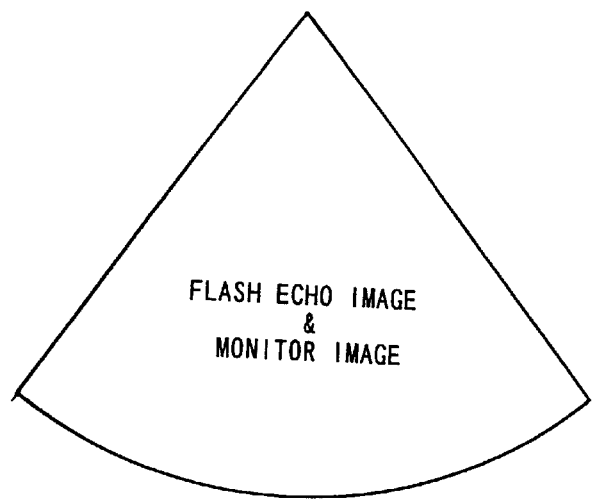
FIG. 20 depicts display examples of images resulting from flash transmission and images resulting from monitor transmission.
Figure 20:
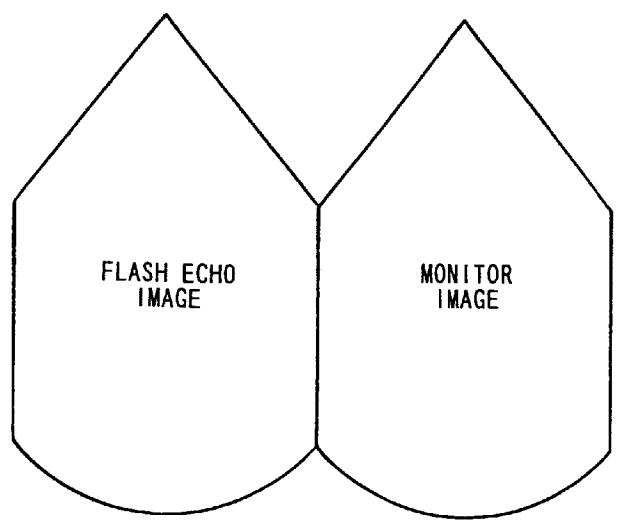
Figure 21:
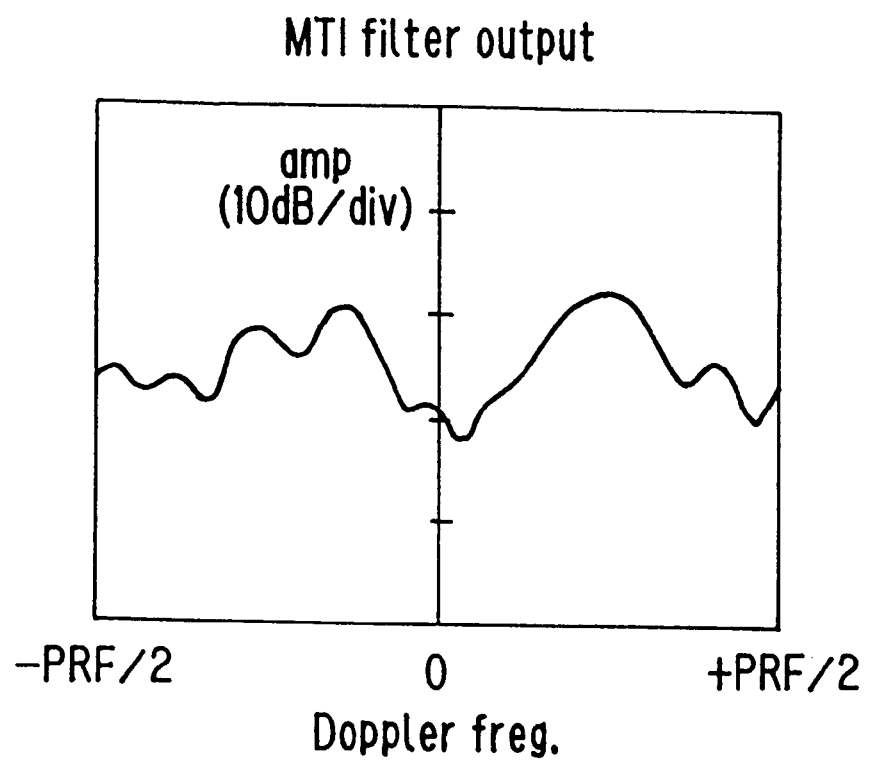
FIG. 21 shows one example of a Doppler spectrum in flash echo imaging.

When the monitor transmission on/off signal represents an off-state (stop) of the monitor transmission, this generator 24G performs the totally same operation as that in the second embodiment. In contrast, in cases the signal represents an on-state of the monitor transmission (the performance of the monitor transmission), an operation shown in FIG. 19 is performed, where flash-transmission transmission-trigger drive pulses P3 are provided to the transmission trigger generator 21 during on-intervals T1 of the flash transmission, as described before, whilst during off-intervals T2 thereof, the operation is switched over according to the type of a monitor mode so as to enable monitor-transmission transmission-trigger drive pulses P3 to be provided to the transmission trigger generator 21.

Figure 7:
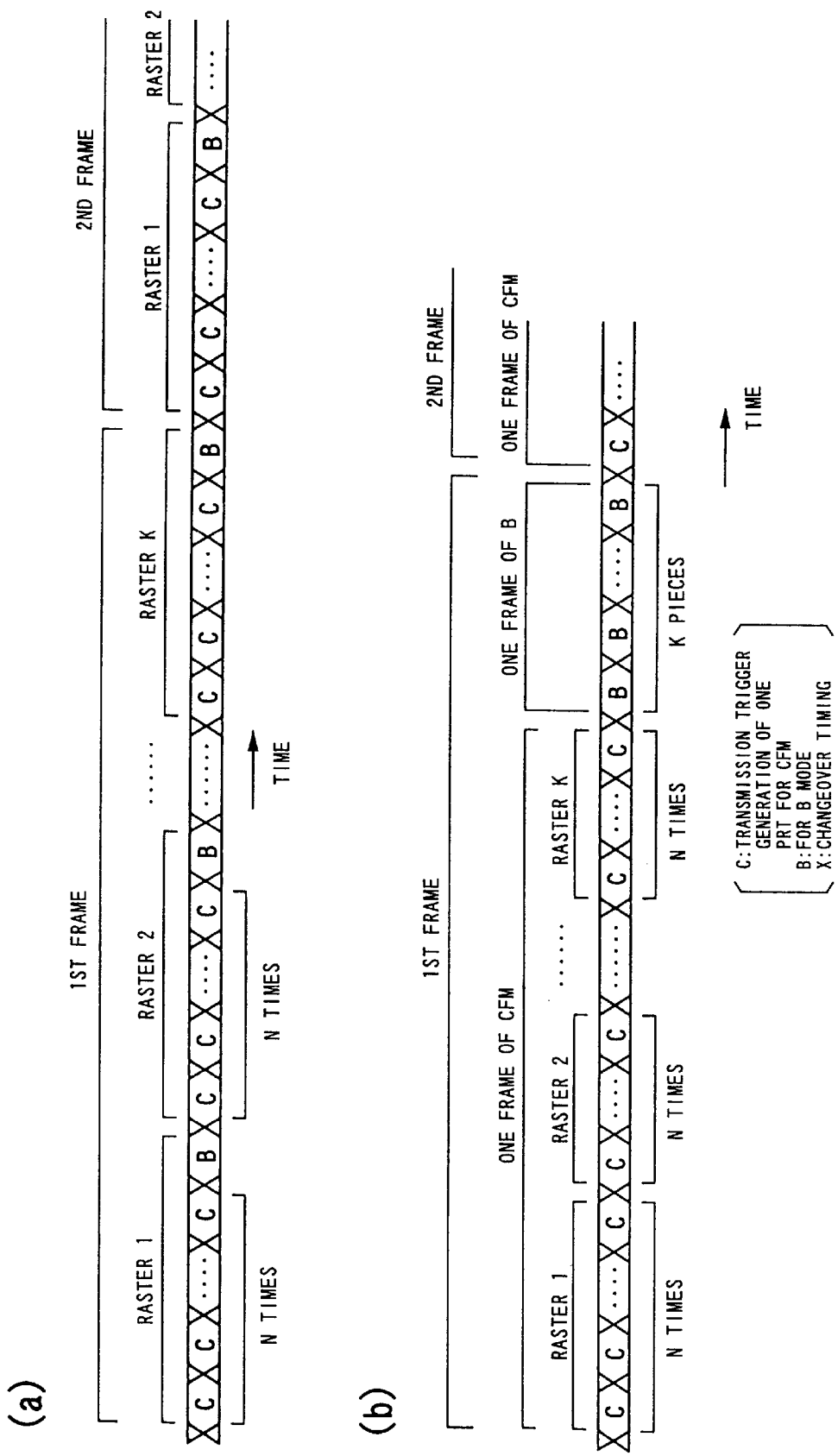
FIG. 7 is an illustration showing a time-sequential order shown by each of a BFM mode and a B mode for a transmission trigger.

When receiving the flash-transmission transmission-trigger drive pulses P3, the transmission trigger generator 21 generates CFM-mode transmission triggers P4 in accordance with the number of specified frames, like the foregoing embodiments. (Preferably, though not shown in FIG. 19, B-mode transmission triggers are also transmitted for obtaining a tomographic image that functions as a background image: Refer to FIG. 7.) In contrast, where receiving the monitor-transmission transmission-trigger drive pulses P3, the transmission triggers are switched to B-mode transmission triggers P4 in accord with an appropriate number of frames that can be worked out through calculation.

Additionally, flash-transmission time setting pulses P2, which are provided by the flash-transmission time setting pulse generator 24F, are supplied to both of the foregoing transmission voltage controller 26 and the transmission channel setting circuit 27 as well as to the preceding transmission trigger drive pulse generator 24G.

The transmission voltage controller 26 controls the values of a drive pulse generated in the transmission circuit 23 in a manner that a transmission sound pressure brought by an ultrasound pulse becomes a first value H during the on-interval T1 of the flash transmission time setting pulse P2, while the transmission sound pressure becomes a second value L during the off-interval T2 thereof. Practically, the voltage of a pulse generated during the on-interval T1 is controlled to a high value, while that during the off-interval T2 to a low value. The transmission channel setting circuit 27 designates the number of transmission channels in the transmission circuit 23, respectively, such that a transmission sound pressure brought by an ultrasound pulse becomes a first value H during the on-interval T1 of the flash transmission time setting pulse P2, while the transmission sound pressure becomes a second value L during the off-interval T2 thereof. In practice, the number of transmission channels during the on-interval T1 is set to a large quantity, whilst that during the off-interval T2 to a small quantity.

The first sound pressure H is determined to a value as large as possible which will cause the flash echo phenomenon of a contrast agent within an allowable range on a regulation toward a living body, although the second sound pressure L is determined to a value less than the first one H. To be specific, the second sound pressure L is set to a low amount at which the contrast agent will not almost cause the flash echo phenomenon. However, if the second sound pressure L is too low, images are difficult to observe because of low sensitivity. Therefore, the pressure L is determined to an amount that will raise sensitivity as high as possible in a range that will not cause the flash echo phenomenon. It is convenient that the second sound pressure L is designated by an operator via the panel switch. In this case, this second sound pressure L manually set is interpreted into the transmission voltage and/or the number of transmission channels, and sent to the controller 26 and/or the setting circuit 27.

In short, it is satisfactory if the transmission sound pressure can be set to the first sound pressure H for the flash transmission (corresponding to the first transmission of the present invention), while to the second sound pressure L for the monitor transmission (corresponding to the second transmission of the present invention). Therefore, either the transmission voltage controller 26 or the transmission channel setting circuit 27 could be used to control the changeover between the first and second sound pressures. In this embodiment, both circuits 26 and 27 operate together so as to change over those sound pressures depending on the transmission modes.

This configuration is able to change over the transmission voltage to either the first sound pressure H or the second sound pressure L depending on the flash and monitor transmission intervals within each one sequence. The first sound pressure is capable of bring about the flash echo phenomenon to obtain a flash echo signal. That is, scanning is performed during this interval on the basis of the totally same time and condition as those in the flash transmission explained in the second embodiment.

In contrast, during the intervals where the flash transmission was turned off in the second embodiment, the voltage is changed over to the second sound pressure L of which quantity is low, and the monitor transmission is continued. Because the second sound pressure is set, the flash echo phenomenon will not occur, even though a full charge of microbubbles. An echo signal obtained by this monitor transmission is processed by the B-mode processor 14, and displayed by the TV monitor 64 in real time as a B-mode tomographic image of a scanned cross section.

In this way, when the flash transmission is designated, the transmission that will cause the flash echo phenomenon is performed, with the result that a CFM-mode image on the flash echo imaging is displayed. In contrast, in the case of designation of the monitor transmission, with no flash echo phenomenon caused, an ordinary B-mode image is displayed in real time as a monitor image. Each of the flash transmission and the monitor transmission is carried out one time per one sequence, then this sequence is repeated. Images obtained by both kinds of transmission can be display alternately on the same screen of the TV monitor 64, as shown in FIG. 20(a). Alternatively, both images could be displayed on separate screens, as shown in FIG. 20(b).

Accordingly, due to the fact that a diagnostic region of an object can be monitored in real time even during intervals where the flash transmission is at rest, it is easier to determine scanning positions. That is, positional shifts, which might occur, between the probe and an object can easily be corrected. To prevent and correct such positional shifts increase reliability for diagnosis with the help of images, not limited to less operational work and shortened time of diagnosis. On one hand, with regions to be imaged observed in real time, a contrast examination on the flash echo imaging can be done. There is therefore provided a simple, easy to operate, and improved-performance diagnostic ultrasound apparatus.

In this embodiment, the monitor transmission is performed in the ordinary B mode, which gives priority to the real-time performance. Alternatively, it is possible to perform the transmission in the CFM mode. If it is desired that flows of blood be observed in color during the monitor, the monitor transmission in the CFM mode is preferred.

Moreover, the foregoing various characteristics of the CFM-mode processor could be practiced into the CFM-mode processor 15 in this embodiment. Those include the configurations where the differentiators are placed instead of the MTI filters and the BPFs are placed before the quadrature phase detector. Further, as described before, it is also possible that the circuitry in which the circuits after the amplifiers in the receiver 13, the B-mode processor 14, and the CFM-mode processor 15 are formed into digital type of circuitry.

Eighth Embodiment

Referring to FIGS. 22 to 25, an eighth embodiment of the present invention will now be described. A diagnostic ultrasound apparatus is directed to imaging that uses more effectively the intervals of the flash transmission "off," which are monitor intervals, though the flash transmission will not be carried out during these intervals, like the seventh embodiment.

Figure 22:
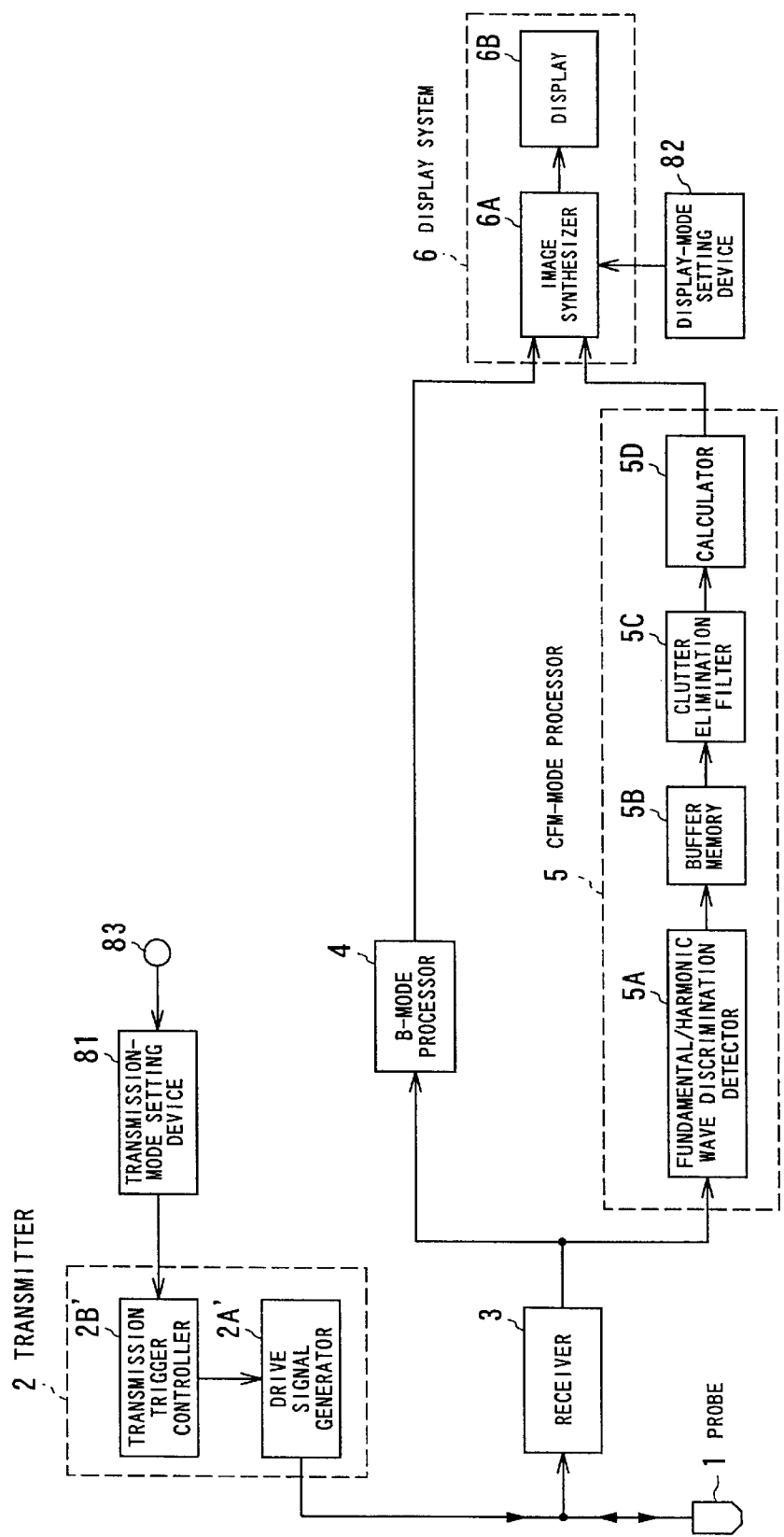
FIG. 22 shows a block diagram of a diagnostic ultrasound apparatus according to an eighth embodiment of the present invention.
Figure 23:
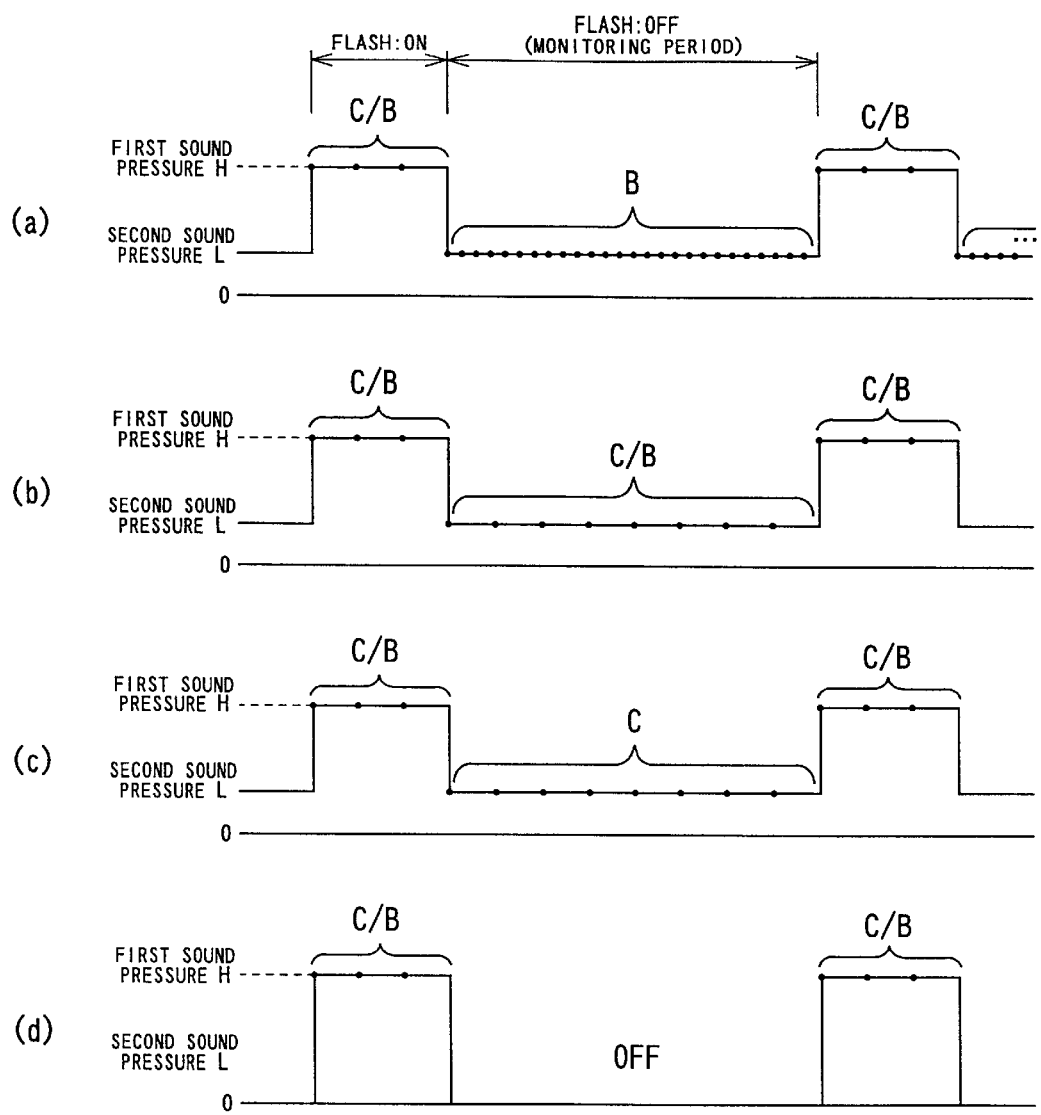
FIG. 23 illustrates types of acquired images and sound pressures in first to fourth transmission modes.

Like the first embodiment, the diagnostic ultrasound apparatus shown in FIG. 22 has, in addition to the probe 1, the transmitter 2 and the receiver 3 both electrically coupled with this probe 1, the B-mode and CFM-mode processors 4 and 5 both electrically coupled with the receiver 3, and the display system 6 electrically coupled with both processors 4 and 5.

As described before, the transmitter 2 has the drive signal generator 2A' and the transmission trigger controller 2B' controlling transmission states via the generator 2A'. Of these, the drive signal generator 2A' is configured identically to a construction in which the transmission trigger generator 21, pulse generator 22, transmission circuit 23, transmission voltage controller 26, and transmission channel setting circuit 27, all of which are shown in FIG. 17, are combined.

The transmission trigger controller 2B' has an identical configuration to the transmission trigger controller 25 shown in FIG. 17. Additionally, the transmission trigger controller 2B' is connected to a transmission-mode setting device 81 from which a transmission mode is issued. A desired transmission mode is designated to the transmission-mode setting device 81 automatically or by hand.

As the transmission mode, as shown in FIGS. 23(a) to (d), four types of modes are prepared. Specifically, a first transmission mode is shown in FIG. 23(a), where the transmission under each of the CFM and B modes is performed for the same specified number of frames during each on-interval of the flash transmission (its transmission sound pressure= the first sound pressure H), while the monitor transmission under only the B-mode is performed at every predetermined period during the monitor interval defined by each off-interval of the flash transmission (its transmission sound pressure=the second sound pressure L).

The transmitting condition of setting the sound pressure to the first quantity H corresponds to the first transmitting condition of the present invention, and that to the second quantity L corresponds to the second transmitting condition thereof. The first and second sound pressures H and L have been described in the foregoing seventh embodiment.

A second transmission mode is shown in FIG. 23(b), where the transmission under each of the CFM and B modes is performed for the same specified number of frames during each on-interval of the flash transmission, while the monitor transmission under each of the CFM and B modes is also performed for the same specified number of frames during the monitor interval defined by each off-interval of the flash transmission.

A third transmission mode is shown in FIG. 23(c), where the transmission under each of the CFM and B modes is performed for the same specified number of frames during each on-interval of the flash transmission, while the monitor transmission under only the CFM is performed at every predetermined period during the monitor interval defined by each off-interval of the flash transmission.

Still, a fourth transmission mode is shown in FIG. 23(d), where the transmission under each of the CFM and B modes is performed for the same specified number of frames during each on-interval of the flash transmission, while the monitor transmission is not performed during the monitor interval defined by each off-interval of the flash transmission (that is, the transmission sound pressure=zero).

Accordingly, even if any transmission mode is designated, the intervals of the flash transmission on-state are occupied by the ultrasound pulse transmission under both modes, and the intervals of its off-state is occupied by the monitoring ultrasound pulse transmission under a designated mode (the first to third transmission modes) or is ordered to the halt of the transmission (the fourth transmission mode).

Like the foregoing embodiments, an echo signal associated with the B-mode transmission is received and processed by the B-mode processor 4, though that associated with the CFM-mode transmission is received and processed by the CFM-mode processor 5.

Figure 24:
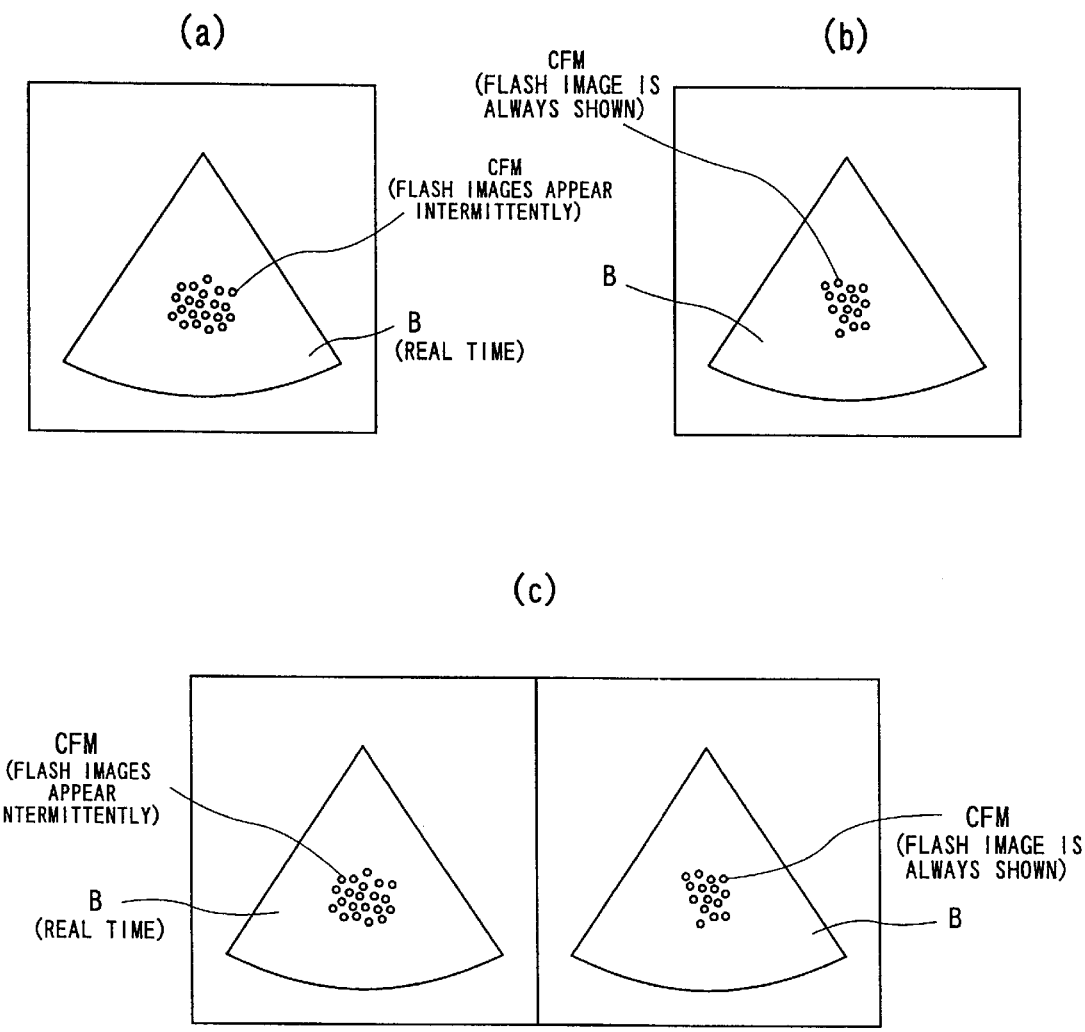
FIG. 24 illustrates several screens for explaining first to third display modes.
Figure 25:
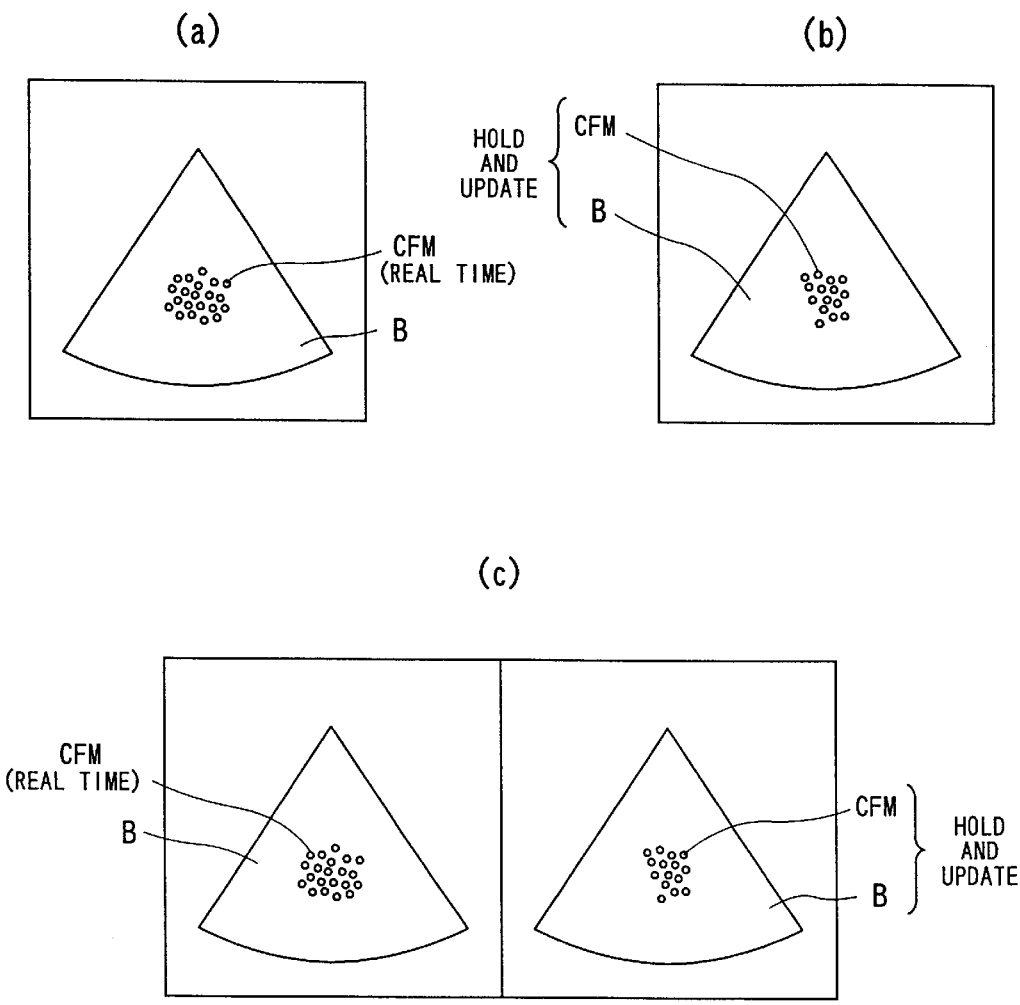
FIG. 25 illustrates several screens for explaining fourth to sixth display modes.

The display system 6 has the image synthesizer 6A synthesizing image data sent from both B-mode and CFM-mode processors and a display 6B displaying the synthesized image data. A display-mode setting device 82 is coupled with the image synthesizer 6A, in which commands representing various types of display modes shown in FIGS. 24 and 25 are appropriately issued from the setting device 82 to the synthesizer 6A. A desired display mode is set to the display-mode setting device 82 in hand or automatically.

When the first to third transmission modes are designated (refer to FIGS. 23(a) to (c)), any display mode selected from a first to third display modes (refer to FIGS. 24(a) to (c)) and a fourth to sixth display modes (refer to FIGS. 25(a) to (c)) is ordered. Further, in the case that the fourth transmission mode is designated (refer to FIG. 23(d)), an appropriate display mode is ordered (refer to FIGS. 24(a) and (b) and FIGS. 25(a) and (b)).

The first display mode is a mode shown as FIG. 24(a), where a color image of blood flows (CFM image) functioning as a first image, which is obtained based on phase displacement information of an echo signal, is superposed on a B-mode image (image indicative of tissue shapes or blood flow states) functioning as a second image, which is obtained almost in real time in the form of dynamic images based on echo signal intensities. The color image is intermittently superposed on the B-mode image in the case that the first transmitting condition is given. The second display mode is a mode shown in FIG. 24(b), in which a blood flow color image (CFM image) acquired under the first transmitting condition is always superposed on a B-mode image with the color image updated. Further, the third image mode is shown in FIG. 24(c), in which both images obtained in both of the first and second display modes are concurrently displayed side by side.

Moreover, the fourth display mode is a mode, as shown in FIG. 25(a), where a blood flow color image (CFM image), which is obtained approximately in real time, is superposed on a B-mode image. The fifth display mode is exemplified in FIG. 25(b), in which a blood flow color image (CFM image) is superposed on a B-mode image in a held condition. This held display condition continues from a monitor interval defined by the flash transmission "off" to the production of the first frame of image in a certain interval of the flash transmission which immediately follows. Every time when the first frame of image is produced, the superposing image is updated. Further, the sixth image mode is shown in FIG. 25(c), in which both images obtained in both of the fourth and fifth display modes are concurrently displayed side by side.

Accordingly, this embodiment enables a plurality of types of transmission modes and a plurality of types of display images to be combined appropriately for imaging during the monitor intervals, thus monitor images of which information is abundant being provided. This makes it possible that images on flash echo imaging are observed totally with consideration of changes in tissue shapes (in the case of the ordinary B mode) during the monitor intervals with no flash transmission or blood flow states including perfusion (in the case of a harmonic B mode or the CFM mode).

In the above embodiment, the transmission trigger controller 2B' could be configured such that it generates a trigger commanding a predetermined transmission mode, without using the transmission mode setting device 81. Similarly, the image synthesizer 6A could be configured so that it performs image synthesis under a predetermined display mode, without using the display-mode setting device 82. Although these configurations require the transmission mode and display mode for the monitor images to be fixed, the apparatus can be simplified in construction.

Furthermore, to the construction in the eighth embodiment, another construction where memory means memorizing Doppler signals in a time-sequential input order thereof, reading means reading the Doppler signals from the memory means at every position of a cross section in the opposite time-sequential order to the input order, and clutter elimination means eliminating clutter components from the Doppler signals read by the reading means, which are described before, could also be applied. In this case, the clutter elimination means could include means for disposing of, after eliminating the clutter components, data influenced by a transmit response occurring in the elimination. Further, the construction of this embodiment may include analysis means for frequency-analyzing the Doppler signals processed by the clutter elimination means, and this analysis means could include means re-designating the signs of the analyzed results. Furthermore, the construction of this embodiment could have means for re-arranging the time sequence of each Doppler signal processed by the clutter elimination means, at every position of the cross section, into a time sequence along its input order, and means for frequency-analyzing the re-arranged Doppler signal.

The techniques that explained in the foregoing third to seventh embodiments, that is, the use of the differentiators substituting for the MTI filters, the extraction of a harmonic from a contrast agent by the BPFs in the CFM-mode processor, and others can be applied to this eighth embodiment as well.

Still, CFM images displaying dynamics of blood flows in color are not confined to two-dimensional color mapping images of velocities of blood flows or a contrast agent (in a contrast echo method), but could be applied to two-dimensional color mapping images of its power amounts and a grayscale image, that is, B-mode angiography image (a section and blood flows are both displayed in gray scales).

Still, the blood flow color image and B-mode image displayed in this embodiment could be images of the fundamental wave of a transmitted ultrasound pulse, images of its harmonic, or images produced by a pulse inversion method (including a pulse inversion Doppler method). Depending on the type of an image, filter means (not shown) capable of passing a desired frequency component of an echo signal could be disposed in both the detector 5A of the CFM-mode processor 5 and the B-mode processor 4. The filters used in both modes may be integrated and arranged into the receiver 3. A desired frequency component, a fundamental wave, a harmonic, and a mixed wave thereof can be used.

Additionally, both of the flash-on intervals and the flash-off intervals (monitor intervals) may consist of unequal intervals, as described before. A period composed of one flash-on interval and one flash-off interval may be adjusted by period adjusting means 83 (refer to FIG. 22) adjustable by hand or programmable. This makes it possible to designate an appropriate monitor interval in accord with blood flow velocities, thus satisfying observation of perfusion in the cardiac muscle or quantification of blood flow dynamics.

Preferably, this period adjusting means 83 are configured in such a manner that it designates the periods in response to an inner trigger generated by a clock incorporated in this apparatus or an outer trigger such as an ECG-synchronized signal. Further, it is preferred that this means 83 selectively change over both types of triggers.

Moreover, in the case that the CFM-mode and B-mode images are acquired in parallel, a plurality of times of transmission carried out for acquiring the CFM-mode image can be used, in part, for producing the B-mode image. This eliminates the necessity of transmission dedicated to the B mode, thus providing an improved frame rate of the images.

The various embodiments according to the present invention have been described as above, so their representative advantages can be summarized as follows.

Because the transmission and reception is controlled to automate the on/off changeovers of generation of the transmission trigger, a CFM image based on an effective flash echo signal is readily obtained, thus providing a practical diagnostic ultrasound apparatus.

Because of controlling the order of transmission, the transmission triggers in the CFM mode precedes those in the B mode. A flash echo image of higher sensitivity can therefore be obtained in the CFM mode.

In cases MTI filters are arranged into means for discriminating a signal from a contrast agent from others, signals received with a plurality of times of transmission and reception can be inputted into the MTI filters in the opposite order to the reception order. Hence, sensitive flash echo data in the CFM mode, which are acquired in an earlier stage, can be used to produce a higher-quality and higher-diagnostic-performance flash echo image.

Further, in the case that means for differentiating adjoining signals among a plurality of signals received with a plurality of times of transmission and reception are arranged into means for discriminating a signal from a contrast agent from others, at least two times of transmission and reception are enough for the elimination of a clutter component. Therefore, CFM flash echo data having a higher real-time capability, which are more sensitive thanks to acquisition in an earlier stage thereof, can be used to produce a CFM-mode flash echo image having a higher sensitivity.

In the case of using a fundamental wave, a CFM-mode flash echo image can be obtained most sensitively, while in the case of using a harmonic, a capability to eliminate artifacts is raised and a higher-quality and higher-diagnostic-performance image can be obtained. Alternatively, the fundamental wave or the harmonic can be used selectively.

Moreover, even a waiting state in which the flash echo phenomenon is not caused, an object's region to be diagnosed can be monitored in real time with monitor images. Accordingly, it is easier to locate a region to be examined, in addition to offering resistance to positional shifts of the probe. Further, with a region to be diagnosed observed in real time, a flash echo contrast examination can be conducted, so a simplified-operation and easy to operate diagnostic ultrasound apparatus with an improved diagnostic performance is provided.

Further, since a variety of techniques of acquiring this monitor image are prepared, an operator is able to observe an monitor image most appropriate for the states of a region to be diagnosed.

The present invention is not restricted to the foregoing embodiments and is practicable in further modified or combined manners without departing from the scope of the gist thereof.

According to the foregoing embodiments, flash echo imaging is performed with the first and second transmitting conditions controlled and the first and second images acquired respectively under those transmitting conditions are displayed in an appropriate fashion. Thus, regardless of whether the flash echo phenomenon is cause or not, image information can effectively be provided in the most proper mode over the whole flash echo imaging. A diagnostic ultrasound apparatus most suitable for the flash echo imaging can therefore be provided.

Additionally, a construction is employed which monitors an object's region to be diagnosed in real time during intervals with no flash echo phenomenon, so that provided is a diagnostic ultrasound apparatus that has upgraded functions and performances of practicality in observing CFM images on flash echo imaging requiring a contrast agent to be injected into an object, a superior maneuverability, and a higher diagnostic performance.

Furthermore, due to the fact that various signals in the CFM mode are processed in the most suitable way to detection of the flash echo phenomenon, there can be provided a diagnostic ultrasound apparatus excellent in sensitivity of detecting a flash echo signal and processing.

What we claim is:

1. A diagnostic ultrasound apparatus for imaging an object into which an ultrasound contrast agent is injected, the apparatus comprising:

an ultrasound transducer for transmitting and receiving an ultrasound pulse to and from the object;

transmitting means for transmitting the ultrasound pulse into the object by driving the ultrasound transducer under a first transmitting condition giving a first destruction capability to the ultrasound contrast agent, and a second transmitting condition giving the ultrasound contrast agent a second destruction capability that is lower than the first destruction capability;

first image producing means for receiving an ultrasound echo of the ultrasound pulse transmitted under the first transmitting condition and for producing a first color-displayed image based on phase displacement information about the ultrasound echo;

second image producing means for receiving an ultrasound echo of the transmitted ultrasound pulse and for producing a second image based on amplitude information about the ultrasound echo; and means for displaying both the first and second images.

2. A diagnostic ultrasound apparatus for imaging an object into which an ultrasound contrast agent is injected, the apparatus comprising:

an ultrasound transducer for transmitting and receiving an ultrasound pulse to and from the object;

transmitting means for transmitting the ultrasound pulse into the object by driving the ultrasound transducer under a first transmitting condition giving a first destruction capability to the ultrasound contrast agent, and a second transmitting condition giving the ultrasound contrast agent a second destruction capability that is lower than the first destruction capability;

first image producing means for receiving an ultrasound echo of the ultrasound pulse transmitted under the first and second transmitting conditions and for producing a first color-displayed image based on phase displacement information about the ultrasound echo;

second image producing means for receiving the ultrasound echo and for producing a second image based on amplitude information about the ultrasound echo; and means for displaying both the first and second images.

3. A diagnostic ultrasound apparatus for imaging an object into which an ultrasound contrast agent is injected, the apparatus comprising:

an ultrasound transducer for transmitting and receiving an ultrasound wave to and from the object;

transmitting means for transmitting the ultrasound pulse into the object by driving the ultrasound transducer under a first transmitting condition giving a first destruction capability to the ultrasound contrast agent, and a second transmitting condition giving the ultrasound contrast agent a second destruction capability that is lower than the first destruction capability;

first image producing means for receiving an ultrasound echo of the ultrasound pulse and for producing a first color-displayed image based on phase displacement information about the ultrasound echo;

second image producing means for receiving an ultrasound echo of the ultrasound pulse transmitted under the first transmuting condition and for producing a second image based on amplitude information about the ultrasound echo; and means for displaying both the first and second images.

4. A diagnostic ultrasound apparatus for imaging an object into which an ultrasound contrast agent is injected, the apparatus comprising:

an ultrasound transducer for transmitting and receiving an ultrasound pulse to and from the object;

a transmitting unit configured to transmit the ultrasound pulse into the object by driving the ultrasound transducer under a first transmitting condition giving a first destruction capability to the ultrasound contrast agent, and a second transmitting condition giving the ultrasound contrast agent a second destruction capability that is lower than the first destruction capability;

a first image producing unit configured to receive an ultrasound echo of the transmitted ultrasound pulse and to produce a first color-displayed image based on phase displacement information about the ultrasound echo;

a second image producing unit configured to receive an ultrasound echo of the ultrasound pulse transmitted under the first transmuting condition and to produce a second image based on amplitude information about the ultrasound echo; and a display unit configured to display both the first and second images.

5. The diagnostic ultrasound apparatus of claim 4, wherein:

the second image producing unit is configured to produce the second image in the form of dynamic images; and the display unit is configured to display the first image intermittently on the second image.

6. The diagnostic ultrasound apparatus of claim 4, wherein:

the display unit is configured to display an image in which the first image is shown without intermissions on the second image.

7. The diagnostic ultrasound apparatus of claim 4, wherein:

the second image producing unit is configured to produce the second image in the form of dynamic images; and the display unit is configured to display the first image intermittently on the second image and to display without intermissions the first image on the second image.

8. The diagnostic ultrasound apparatus of claim 4, wherein:

the first image producing unit is configured to produce the first image in real time; and the display unit is configured to display the real-time first image on the second image.

9. The diagnostic ultrasound apparatus of claim 4, wherein:

the display unit is configured to display an image in which the first image is superposed on the second image and to update the superposed first image every predetermined frame-th image corresponding to a predetermined number-th ultrasound transmission under the first transmitting condition.

10. The diagnostic ultrasound apparatus of claim 4, wherein:
the first image producing unit is configured to produce the first image in real time; and
the display unit is configured to simultaneously display both a real-time image in which the real-time first image is superposed on the second image and a hold image in which the first image is superposed on the second image.

11. The diagnostic ultrasound apparatus of claim 4, wherein:
the first image is either an image indicating power of blood flowing in the object or power of the ultrasound contrast agent or an image of motion velocities of the blood flow.

12. The diagnostic ultrasound apparatus of claim 4, wherein either the first or second image is selected from a group of images including:
an image of a fundamental wave of the ultrasound pulse,
an image of a harmonic wave of the ultrasound pulse, and
a pulse inversion image formed by transmitting and receiving the ultrasound pulse based on a pulse inversion technique.

13. The diagnostic ultrasound apparatus of claim 4, wherein the transmitting unit is configured to order a period including:
an ultrasound transmission interval under the first transmitting condition, and
an ultrasound transmission interval under the second transmitting condition, to repeat at either equal intervals or unequal intervals.

14. The diagnostic ultrasound apparatus of claim 13, further comprising:
an ordering unit configured to manually or programmably order at least part of pieces of information including the period and the first and second transmitting conditions.

15. The diagnostic ultrasound apparatus of claim 13, wherein the transmitting unit includes:
an element configured to set the period to correspond to either an inner trigger incorporated in the apparatus or an outer trigger given to the apparatus; and
an element configured to order selection of both the inner and outer triggers.

16. The diagnostic ultrasound apparatus of claim 4, wherein the transmitting unit includes:
a transmission-order commanding element configured to always precede transmission of the ultrasound for obtaining the first image to transmission of the ultrasound for obtaining the second image, when the first and second image producing units produce the first and second images in parallel.

17. The diagnostic ultrasound apparatus of claim 16, wherein:
the transmission-order commanding element is configured to command an order of both types of transmission for the first and second images by a unit of a raster or a frame along which the ultrasound pulse is transmitted.

18. The diagnostic ultrasound apparatus of claim 4, wherein:
the second image producing unit is configured to produce the second image using the echo signal obtained by part of the transmission performed by the transmitting unit under the first transmitting condition, when the first and second images are produced in parallel.

19. The diagnostic ultrasound apparatus of claim 4, further comprising:
a filter configured to pass a desired frequency component of the echo signal.

20. The diagnostic ultrasound apparatus of claim 19, wherein the desired frequency component is selected from a group of components including:
a fundamental component,
harmonic component, and
a mixture of the fundamental and harmonic waves of the ultrasound pulse.

21. The diagnostic ultrasound apparatus of claim 19, wherein:
a) the transmitting unit is configured to scan a cross section of the object with the ultrasound pulse transmitted in a same direction a plurality of times in order to produce the first image; and
b) the first image producing unit includes:
an element configured to receive the echo signal generated by the scanning,
an element configured to produce from the received echo signal, a data train including a plurality of pieces of data in line in a time-sequence direction at each sampled spatial position in the cross section,
an element configured to extract a phase displacement component from the data train, and
an element configured to produce the first image from the phase displacement component.

22. The diagnostic ultrasound apparatus of claim 19, wherein:
the first image producing unit includes an element for extracting the phase displacement information by either high pass filtering or difference processing.

23. The diagnostic ultrasound apparatus of claim 22, wherein the extracting element for the phase displacement information is configured to perform the high pass filtering, and includes:
a unit configured to provide each of data composing the data train with the high pass filtering in an opposite time sequential order to an acquisition order of the data,
a unit configured to remove, from the high pass filtered data, data exerted by a transit response due to the high pass filtering, and
a unit configured to restore the time sequential order of remaining data formed by the removing processing to the original acquisition order thereof.

24. The diagnostic ultrasound apparatus of claim 22, wherein the extracting element for the phase displacement information is configured to perform the high pass filtering, and further includes:
a unit configured to provide each of data composing the data train with the high pass filtering in an opposite time sequential order to an acquisition order of the data,
a unit to configured to remove, from the high pass filtered data, data exerted by a transit response due to the high pass filtering, and
a unit configured to reverse a sign representing directions of velocity for a velocity image associated with remaining data formed by the removing processing.

25. The diagnostic ultrasound apparatus of claim 4, wherein:
the second image producing unit is configured to receive the ultrasound echo of the ultrasound pulse transmitted under both the first and second transmitting conditions to produce the second image based on the amplitude information about the ultrasound echo.

26. A diagnostic ultrasound apparatus for imaging an object into which an ultrasound contrast agent is injected, the apparatus comprising:

an ultrasound transducer for transmitting and receiving an ultrasound pulse to and from the object;
   a transmitting unit configured to transmit the ultrasound pulse into the object by driving the ultrasound transducer under a first transmitting condition giving a first destruction capability to the ultrasound contrast agent, and a second transmitting condition giving the ultrasound contrast agent a second destruction capability that is lower than the first destruction capability;
   a first image producing unit configured to receive an ultrasound echo of the ultrasound pulse transmitted under the first transmitting condition and to produce a first color-displayed image based on phase displacement information about the ultrasound echo;
   a second image producing unit configured to receive an ultrasound echo of the transmitted ultrasound pulse and to produce a second image based on amplitude information about the ultrasound echo; and
   a display unit configured to display both the first and second images.

27. The diagnostic ultrasound apparatus of claim 26, wherein:

the second image producing unit is configured to produce the second image in the form of dynamic images; and
   the display unit is configured to display the first image intermittently on the second image displayed in the form of dynamic images.

28. The diagnostic ultrasound apparatus of claim 27, wherein:

the first image is either an image indicating power of blood flowing in the object or power of the ultrasound contrast agent or an image of motion velocities of the blood flow.

29. The diagnostic ultrasound apparatus of claim 26, wherein:

the first image producing unit is configured to receive the ultrasound echo of the ultrasound pulse transmitted under both the first and second transmitting conditions to produce the first color-displayed image based on the phase displacement information about the ultrasound echo.

30. A diagnostic ultrasound apparatus for imaging an object into which an ultrasound contrast agent is injected, the apparatus comprising:

an ultrasound transducer for transmitting and receiving an ultrasound pulse to and from the object;
   a transmitting unit configured to transmit the ultrasound pulse into the object by driving the ultrasound transducer under a first transmitting condition giving a first destruction capability to the ultrasound contrast agent, and a second transmitting condition giving the ultrasound contrast agent a second destruction capability that is lower than the first destruction capability;
   a first image producing unit configured to receive an ultrasound echo of the ultrasound pulse transmitted under the first and second transmitting conditions and to produce a first color-displayed image based on phase displacement information about the ultrasound echo;
   a second image producing unit configured to receive the ultrasound echo and to produce a second image based on amplitude information about the ultrasound echo; and
   a display unit configured to display both the first and second images.

31. The diagnostic ultrasound apparatus of claim 30, wherein:

the second image producing unit is configured to produce the second image in the form of dynamic images; and
   the display unit is configured to display the first image intermittently on the second image.

32. The diagnostic ultrasound apparatus of claim 30, wherein:

the display unit is configured to display an image in which the first image is shown without intermissions on the second image.

33. The diagnostic ultrasound apparatus of claim 30, wherein:

the second image producing unit is configured to produce the second image in the form of dynamic images; and
   the display unit is configured to display the first image intermittently on the second image and to display without intermissions the first image on the second image.

34. The diagnostic ultrasound apparatus of claim 30, wherein:

the first image producing unit is configured to produce the first image in real time; and
   the display unit is configured to display the real-time first image on the second image.

35. The diagnostic ultrasound apparatus of claim 30, wherein:

the display unit is configured to display an image in which the first image is superposed on the second image and to update the superposed first image every predetermined frame-th image corresponding to a predetermined number-th ultrasound transmission under the first transmitting condition.

36. The diagnostic ultrasound apparatus of claim 30, wherein:

the first image producing unit is configured to produce the first image in real time; and
   the display unit is configured to simultaneously display both a real-time image in which the real-time first image is superposed on the second image and a hold image in which the first image is superposed on the second image.

37. The diagnostic ultrasound apparatus of claim 30, wherein:

the first image is either an image indicating power of blood flowing in the object or power of the ultrasound contrast agent or an image of motion velocities of the blood flow.

38. The diagnostic ultrasound apparatus of claim 30, wherein either the first or second image is selected from a group of images including:

an image of a fundamental wave of the ultrasound pulse,
   an image of a harmonic wave of the ultrasound pulse, and
   a pulse inversion image formed by transmitting and receiving the ultrasound pulse based on a pulse inversion technique.

39. The diagnostic ultrasound apparatus of claim 30, wherein the transmitting unit is configured to order a period including:

an ultrasound transmission interval under the first transmitting condition, and
   an ultrasound transmission interval under the second transmitting condition, to repeat at either equal intervals or unequal intervals.

40. The diagnostic ultrasound apparatus of claim 30, wherein the transmitting unit includes:
a transmission-order commanding element configured to always precede transmission of the ultrasound for obtaining the first image to transmission of the ultrasound for obtaining the second image, when the first and second image producing units produce the first and second images in parallel.

41. The diagnostic ultrasound apparatus of claim 30, wherein:
the second image producing unit is configured to produce the second image using the echo signal obtained by part of the transmission performed by the transmitting unit under the first transmitting condition, when the first and second images are produced in parallel.

42. The diagnostic ultrasound apparatus of claim 30, further comprising:
a filter configured to pass a desired frequency component of the echo signal.

43. The diagnostic ultrasound apparatus of claim 30, wherein:
the second image producing unit is configured to receive the ultrasound echo of the ultrasound pulse transmitted under both the first and second transmitting conditions to produce the second image based on the amplitude information about the ultrasound echo.

44. A diagnostic ultrasound apparatus for imaging an object into which an ultrasound contrast agent is injected, the apparatus comprises:
an ultrasound transducer for transmitting and receiving an ultrasound pulse to and from the object;
a transmitting unit configured to transmit the ultrasound pulse into the object by driving the ultrasound transducer under first and second transmitting conditions that differ in respective first and second destruction capabilities given to the ultrasound contrast agent;
a first image producing unit configured to receive an ultrasound echo of the transmitted ultrasound pulse transmitted under the first transmitting condition and to produce a first image based on phase displacement information about the ultrasound echo;
a second image producing unit configured to receive an ultrasound echo of the transmitted ultrasound pulse and to produce a second image based on amplitude information about the ultrasound echo; and
a display unit configured to display both the first and second images in mutually different colors.

45. The diagnostic ultrasound apparatus of claim 44, wherein:
the first destruction capability is lower than the second destruction capability.

46. A diagnostic ultrasound apparatus for imaging an object into which an ultrasound contrast agent is injected, the apparatus comprising:
an ultrasound transducer for transmitting and receiving an ultrasound pulse to and from the object;
a transmitting unit configured to transmit the ultrasound pulse into the object by driving the ultrasound transducer under first and second transmitting conditions that differ in respective first and second destruction capabilities given to the ultrasound contrast agent;
a first image producing unit configured to receive an ultrasound echo of the transmitted ultrasound pulse and to produce a first image based on phase displacement information about the ultrasound echo;
a second image producing unit configured to receive an ultrasound echo of the ultrasound pulse transmitted under the first transmuting condition and to produce a second image based on amplitude information about the ultrasound echo; and
a display unit configured to display both the first and second images in mutually different colors.

47. The diagnostic ultrasound apparatus of claim 46, wherein:
the first destruction capability is lower than the second destruction capability.

* * * * *